United States Patent [19]
Gibbs et al.

[11] Patent Number: 5,829,438
[45] Date of Patent: Nov. 3, 1998

[54] SYSTEM AND METHOD FOR THE INFUSING OF TOCOLYTIC DRUGS IN RESPONSE TO THE ONSET OF PREMATURE LABOR DETECTED BY ULTRASONIC MONITORING OF THE DILATATION AND/OR EFFACEMENT OF THE CERVIX OS

[76] Inventors: David L. Gibbs; Michael Harrison, both of c/o UCSF Fetal Treatment Center, 1601 Health Sciences West, 3rd and Parnassus, San Francisco, Calif. 94143; W. Scott Kemper, 3334 Buena Vista St., San Diego, Calif. 92109; Michael P. Guberek, 426 Jolina Way, Encinitas, Calif. 92024

[21] Appl. No.: 514,234

[22] Filed: Aug. 7, 1995

Related U.S. Application Data

[63] Continuation-in-part of Ser. No. 322,613, Oct. 12, 1994, Pat. No. 5,438,996.

[51] Int. Cl.⁶ ........................................................ A61B 8/00
[52] U.S. Cl. ........................................ 128/775; 128/660.02
[58] Field of Search ........................ 128/661.07, 660.06, 128/660.02, 662.03, 661.02, 675, 774, 775, 778; 424/608; 514/509, 565, 608

[56] References Cited

U.S. PATENT DOCUMENTS

| | | | |
|---|---|---|---|
| 5,406,961 | 4/1995 | Artal | 128/778 |
| 5,438,996 | 8/1995 | Kemper et al. | 128/661.02 |
| 5,508,045 | 4/1996 | Harrison et al. | 424/608 |

*Primary Examiner*—George Manuel
*Attorney, Agent, or Firm*—Fuess & Davidenas

[57] ABSTRACT

The onset of spontaneous abortion or premature labor of a pregnant human female is continuously monitored, potentially for periods of several months and longer, by a real-time transit-time ultrasonic monitor of the dilatation and/or effacement of the cervix os, preferably by a computerized ambulatory monitor. The preferred computerized monitor sounds an alarm upon the detection of variably present conditions, normally the compound conditions of five or more 10% cyclical variations in the dilatation or effacement of the cervix os within a period of one hour, coupled with a greater than 1 centimeter increase over baseline of either dilatation or effacement, which compound conditions normally indicate the early onset of labor. The monitor connects to an infusion pump, likewise preferably ambulatory, for directing and controlling the infusion of one or more tocolytic, labor-preventing, drugs if labor continues. In this manner patient activity and patient chemistry can be early detected, early alarmed and early beneficially altered even before it is possible to receive the diagnosis or treatment of a physician of other health care provider.

23 Claims, 12 Drawing Sheets

ADVANTAGES AND DISADVANTAGES OF DIGITAL CERVIMETRY METHODS

| | Digital Cervimetry | Mechanical Cervimetry | Magnetic Cervimetry | Previous Ultrasonic Cervimetry | Present Invention Cervimetry |
|---|---|---|---|---|---|
| Installation | Easy | Difficult | Difficult | Difficult | Difficult |
| Patient comfortable during installation | No | No | No | No | No |
| Patient comfortable after installation | Yes | No | Yes | Yes | Yes |
| Convenience | High | Low | Moderate | Moderate | High |
| Measurement by Stretching | Yes | Yes | No | No | No |
| Possibility of Digital Pelvic Examination | Yes | No | Diminished | Diminished | Slightly Diminished |
| Output Stability | Subjective | Calipers moveable (1) | Relies on signal intensity (2) | Relies on signal transit time; good | Relies on signal transit time; good |
| Output Linearity | Subjective | Yes, almost | Yes (3) | Yes | Yes |
| Recording up to full dilatation | Yes | No; limited (4) | Not always (5) | Yes | Yes |
| Patient Ambulatory | No | No | No | No | Yes |
| Monitoring, with History | No | No | No | Limited | Total |
| Monitoring, with Alarm | No | No | No | Yes | Yes |

Figure 1

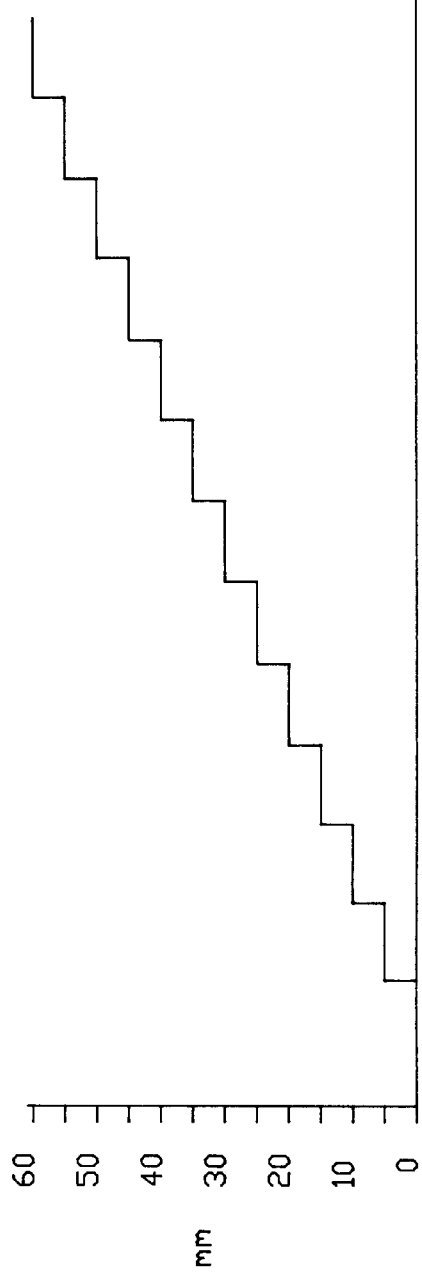
Fig. 5a CALIBRATION
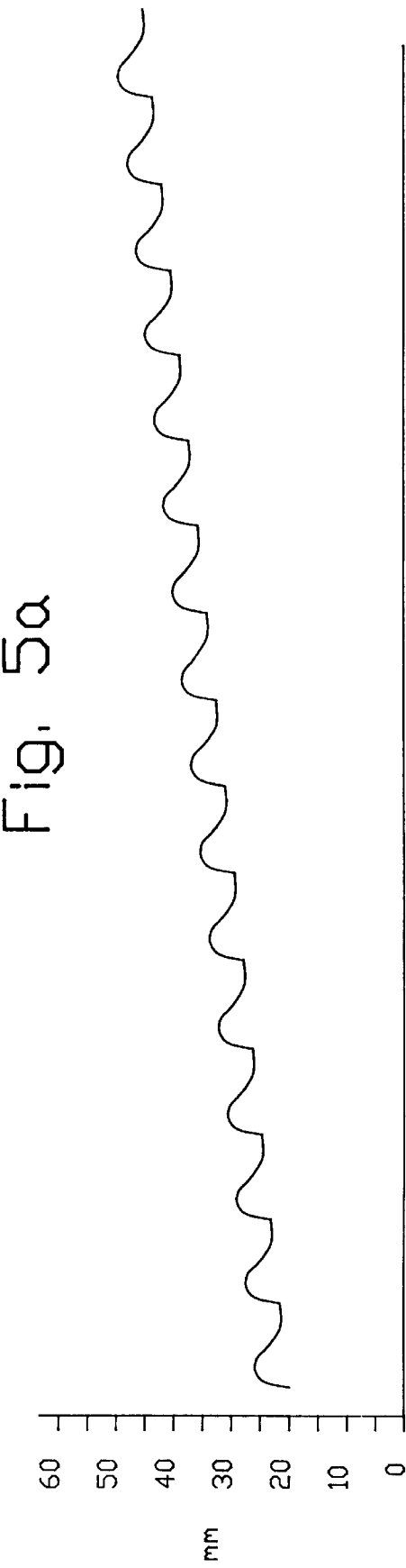
Fig. 5b CERVICAL DIAMETER

SYSTEM AND METHOD FOR THE INFUSING OF TOCOLYTIC DRUGS IN RESPONSE TO THE ONSET OF PREMATURE LABOR DETECTED BY ULTRASONIC MONITORING OF THE DILATATION AND/OR EFFACEMENT OF THE CERVIX OS

REFERENCE TO RELATED APPLICATIONS

The present application is a Continuation-in-Part of U.S. patent application Ser. No. 08/322,613 filed Oct. 12, 1994, for an AMBULATORY, ULTRASONIC TRANSIT TIME, REAL-TIME, CERVICAL EFFACEMENT AND DILATATION MONITOR WITH DISPOSABLE PROBES issued Aug. 8, 1995, as U.S. Pat. No. 5,438,996. This predecessor application and patent is to the selfsame inventors W. Scott Kemper and Michael P. Guberek who are included among the co-inventors of the present application.

The present application is a companion to U.S. patent application Ser. No. 08/512,333 for a DEVICE FOR HOLDING MEDICAL INSTRUMENTATION SENSORS AT AND UPON THE CERVIX OS OF A HUMAN FEMALE, PARTICULARLY FOR HOLDING THE ULTRASONIC TRANSDUCERS OF AN ULTRASONIC TRANSIT TIME, REAL-TIME, CERVICAL EFFACEMENT AND DILATATION MONITOR filed on an even date herewith. The related application is to inventors including the selfsame Michael Harrison, W. Scott Kemper and Michael P. Guberek who are included among the co-inventors of the present application.

The contents of the predecessor and of the companion patent applications are incorporated herein by reference.

BACKGROUND OF THE INVENTION

1. Field of the Invention

The present invention generally concerns systems and methods for automatically administering tocolytic, labor-preventing, drugs in order to prevent the premature onset of labor and to prolong gestation so that the mortality, and complications, of premature childbirth may be, insofar as is possible, avoided.

The present invention particularly concerns the automated administration of tocolytic drugs in response to detection of the commencement of earliest stages of labor by use of a real-time, transit-time, ultrasonic monitor—including an ambulatory version of such monitor—of the dilatation and/or effacement of the cervix os of a pregnant human female.

2. Description of the Prior Art

The avoidance of spontaneous abortion and premature labor, and the prolongation of gestation, in human females is desirable for many very important reasons. Gestation is desirably prolonged for variously increasing minimum periods in order to (i) make more probable a viable live birth, (ii) reduce the incidence of health complications attending a prematurely born child, and (iii) reduce the time period during which a premature infant, even if healthy, must, because of its size and viability, receive extraordinary care. All the factors of (i) live birth, (ii) a healthy child, and (iii) a child that can timely leave the hospital in the custody of its parent(s), obviously have an impact on the happiness and well-being of the parents and relatives. There is also and impact on society from premature births, including a very great societal economic impact in caring for children who are delivered greatly prematurely.

Fortunately, there is a class of drugs call tocolytic, or labor-preventing, drugs that are effective to postpone labor. Typical tocolytic drugs included Ritodrine and Terbutaline, which are beta-sympathomimetic. However, these drugs must generally, in order to be effective, be administered before the full onset of labor, and are of uncertain efficacy or safety if administered after full blown labor has begun.

Although tocolytic drugs are sometimes continuously administered at low levels to a pregnant woman, normally by infusion, during the duration of a high risk period of her pregnancy, normally between about twenty-eight and thirty-four weeks gestation (28–34 weeks), the drugs have undesirable side effects upon renal function, respiratory function, heart rate and general body musculature tone. Dosages must remain low, typically now more than 0.1 cc per hour of 1 mg/cc solution Terbutaline. The effectiveness of these low dosages in avoiding the onset of labor is inconsistent, and poorly quantified.

Perhaps the best data exists concerning the postponement of labor resulting from the special case of a surgical operation upon the fetus. If nothing preventative is done an operation upon the fetus will invariably induce labor. Typically Indomethacin—a non-steroidal drug serving to decrease prostaglandin synthesis and to decrease any prostaglandin cascade leading to labor—is administered orally or rectally both pre- and post-operation. Indomethacin is not suitable for administration longer than several days because it induces renal failure in the fetus. Intravenous magnesium—which serves as a direct acting muscle relaxant—is also administered post operatively, typically for a week or so until the respiratory depression induced in the mother is no longer tolerable. Finally, a tocolytic drug, typically Terbutaline, is typically started some days after the operation, often at the time that magnesium is discontinued. All the best and most advanced pharmacological regimens that can be given, circa 1995, will typically hold off labor in about 90% of the pregnancies for a week or two after an operation on the fetus, but seldom longer than that. The body seems to build up an immunity to the function of the drugs.

The response of a pregnant woman whose fetus is at strong risk of premature delivery by virtue of having been operated on to tocolytic drugs may, or may not, be analogous to the response of a woman who, for essentially unknown reasons, is biologically disposed to premature labor. However, since the tocolytic drugs are expected to function the same in the bodies of both such women, it is useful to assess just what, and what cannot, be done to postpone labor in the more consistent, and predictable, cases of women who have incurred an operation on their unborn child. These later case shown that it is difficult, if not impossible, to control the onset of labor over a long, multi-week and multi-month, period simply by the use of drugs.

It will further be understood that a continuous maintenance of a pregnant woman and her fetus on labor-preventing drugs for so long as is the multi-month period during which labor and childbirth would presently desirably be postponed is presently, circa 1995, would be hazardous, with likely adverse health consequences to the mother and the fetus. Finally, tocolytic drugs are of only modest, and apparently decreasing, effectiveness when used continuously.

Accordingly, it would be most desirable to use tocolytic drugs only if and when required, namely when the woman's body is about to enter true labor. When it is considered that some of the patients on which these drugs may be used as a precaution might not have, in actual fact, suffered premature labor if no drugs at all had been used, the desirability of not administering tocolytic drugs unless they actually become required is accentuated.

The best way of postponing premature labor is to very timely detect the early onset of labor, and to very timely administer a tocolytic drug, normally all within a period of one hour or, preferably, even less. The detection of labor is commonly by (i) the woman's reporting, and the physician's observation of, uterine contractions, in combination with (i) cervical dilatation or effacement. Uterine contractions alone are quite common, and an unreliable single indicator of the onset of actual labor. If nothing is done to suppress labor once it is detected as giving rise to both (i) uterine contractions and (ii) cervical dilatation/effacement, it invariably proceeds.

If, however and by example, an injection of 0.5 cc of 1 mg/cc Terbutaline solution is administered to a pregnant female of 28–34 weeks pregnancy in the first stages of labor, the success rate in avoiding such an escalation of the labor as almost invariably leads to delivery (alternatively, spontaneous abortion), and prolonging pregnancy, is modestly good, and is very roughly estimated to be about 60% successful for pregnancies not otherwise complicated such as by systemic pathological conditions, or trauma to the mother.

There is scant data, and most of that empirical, regarding the relative efficacy of timeliness in the administration of tocolytic drugs. This lack of data exists because (i) pregnant women are seldom in a hospital or other environment where the very earliest onset of true labor can be recognized, (ii) an attending physician may be reticent to diligently proceed at all hours of the day and night, and simply in response to reported "labor pains", to make all such detailed observations over a period of hours as may permit that the onset of true labor can be recognized at the earliest possible moment, and (iii) manual digital methods for detecting the onset of labor effectively demand that labor should be somewhat advanced even before it can be unambiguously recognized with certainty. However, it is known that chemical changes in the woman's body, most notably the prostaglandin cascade, escalate with labor. It is also known that once labor has progressed to a certain point it is essentially irreversible. It seems logical that early intervention is desirable.

As will be further discussed, the cyclical dilatation and effacement of the cervix os of a gravid female appears, circa 1995, to be a useful and non-invasive way of detecting the very earliest onset of labor in mammals, including humans. The cervix os undergoes a cyclical dimensional variation, as well as an overall increase in size, for the duration of human labor, which is typically some hours, culminating in delivery. This dimensional variation may, with appropriate instrumentation and continuous monitoring, be observed to have started at a very particular and precise point in time. There is no known phenomena, either physical or neurological or biochemical, that marks the beginning of human labor any more precisely, any better, or, importantly, any earlier. Accordingly, observation and continuing observation of the cervix os is a very powerful and well established technique, known even to the ancients, for monitoring the onset, and the progress, of labor.

The record short human gestations which have resulted in viable live births are, circa 1995, twenty-six (26) weeks. These exceptionally rare survivals are the subjects of papers in medical journals. The normal period considered the practical minimum for gestation if a live birth is likely realizable in a major medical center is twenty-eight (28) weeks. If the birth transpires in a facility without specialized facilities for the care of premature infants, or in areas of the second or third world where childbirth becomes progressively more hazardous for both the mother and child, the period during which the child is desirably maintained in utero increases all the way to normal full term. Human gestation is desirably extended to thirty-four (34) weeks in order to assure near-normal probability of a viable live birth even under the best, first-world, circumstances. Although the probability of successful delivery, and the good health of the newborn continues to improve (sometimes for reasons more reflective of the overall good health and prenatal care of the mother as opposed simply to the benefit of being longer in the womb) all the way up to the normal full human gestation period of thirty-six to forty (36–40) weeks, active medical intervention is normally not used to postpone labor beyond thirty-four (34) weeks.

Accordingly, human gestation is, if possible and other medical conditions of the pregnant woman not counter-indicating, preferably prolonged as long as about thirty-four (34) weeks, which is considered the lower limit for live birth in advanced modern facilities without appreciably greater complications than are incurred by babies carried to the full normal term of thirty-six to forty (36–40) weeks. If gestation can be prolonged from the practical minimum of twenty-eight (28) weeks at which viable live births routinely transpire in advanced hospitals for only four (4) weeks longer, i.e., to thirty-two (32) weeks, then a cost savings in excess of $100,000 to $300,000 U.S. can typically be realized circa 1995—even over the costs of continuous hospitalization and monitoring of the mother during the critical period. It should be understood that there are some areas of the United States, and most of the world, where neither the quality nor the quantity of resource exists to keep a highly premature infant alive. Although direct financial outlays may be less in these areas, the human cost is very great. People inevitably wishing to have children, and there being no viable way to even certainly detect, let alone prevent the pregnancies of, females at risk for premature delivery, it is thus of consummate interest to prolong, if possible, pregnancies until (usually) near full term.

Cause and constant supervision of high-risk pregnancies has historically involved the use of what were, at the times introduced, new and advanced technologies. This lengthy background has led, culminating in the present and related inventions, to the continuous recording and monitoring of cervical dilatation during labor by means of ultrasonic cervimetry. To support this continuous monitoring, probes must be maintained continuously in position.

The ancients knew that the dilatation of the cervix, discernable with and by the fingers during manual digital assessment, attended the onset of labor in the human female.

2.1 The General History of Cervimeters Including Ultrasonic Cervimeters, and of the Measurements Obtainable With Such Cervimeters Current medical knowledge of cervical behavior descends largely from a huge base of historical data obtained by repeated digital palpation or 'digital cervimetry' during labor. Both vaginal and rectal examination have been used. The latter method was introduced by Kroenig to prevent ascending uterine infection. Reference Kroeig, A. Der Ersatz der inneren Untersuchung Kriessender durch die Unteersuchung per Rectum; *CENTRALBL GYNAKOL* 1894; 18:235–243. Semmelweiss' classic work involving the relationship between vaginal examination and puerperal infection is well appreciated. Reference Semmelweiss, I., in Von Gorky, Y., ed., Semmelweisss gesammte Werke, Jena. 1905, VEB Gustav Fisher Verlag.

Although digital examination offers valuable clinical information on the progress of labor, its intermittent character does not allow an assessment of the dynamics of cervical dilatation. For that reason many attempts have been made to construct devices, cervimeters, for objective and continuous measurement of cervical dilatation based on (electro) mechanical, electronic and ultrasonic principles. A historical overview of some of nineteen various instruments published since the early fifties is presented in the article Assessment of cervical dilatation during labor; a review, by T. vand Dessel, et al. appearing in *EUR. JNL. OBS. GYN. & REP. BIO.* 41 (1991) 165–171.

Instrument-based cervimetry, or cervical dilatation measurement, has in particular been performed by mechanical, magnetic and/or ultrasonic means. A history of instrument-based cervimetry is presented by Moss, P. L., et al. as Continuous cervical dilatation monitoring by ultrasonic methods during labor, appearing in *AM. J. OBSTET. GYNECOL.* 132:16, 1978. The following text is derived from that article.

Moss, et al. point out that Friedman was the author in 1936 of a report discussing mechanical cervimetry. See Friedman, E. A.: Cervimetry, an objective method for study of cervical dilatation in labor, *AM. J. OBSTET. GYNECOL.* 71:1189, 1956. This paper was followed by another paper co-authored with Von Micsky in 1963. See Friedman, E. A., and Von Micsky, L. I.: Electronic cervimeter, A research instrument for the study of cervical dilatation in labor, *AM. J. OBSTET. GYNECOL.* 87: 789.

Siener cooperated with West from 1962 to 1972, and with Krementsoy in 1968, in the use the same method. See Siener, H.: An apparatus for recording the opening of the cervix during labor, *ZENTALBL GYNAEWKOL* 78:2069, 1956; Siener, H.: A new electromechanical apparatus for measuring labor activities by the execution of combination measurements, *ARCH. GYNAEKOL.* 196: 365, 1961; Siener, H.: First stage of labor recorded by cervical tonometry, *AM. J. OBSTET. GYNECOL.* 86:303, 1963; Siener, H. and West, I.: Internal isometry and graphic registration of cervix dilatation as a basis for calculation of labor effectiveness and soft tissue resistance, *GEBURTSHILFE FRAUENHEILKD* 32: 123. 1972; and Krementsoy, U.: Improved technique for measurement of cervical dilatation, *BIOMED. ENG.* (N.Y.) 2:350 1968.

The magnetic cervimeter was first proposed by Smith in 1954. See Smith, C. N.: Measurement of the forces and strains of labor and the action of certain oxytocic drugs, International Congress of Obstetrics and Gynecology, Geneva, 1954, S. A. George, P. 1030. However there were many drawbacks and it was only in 1971 that Rice, and also Kriewall, tried to solve these problems. Reference Rice, D. A.: Mechanism and measurement of cervical dilatation. Doctoral thesis, Purdue University, Lafayette, Ind., 1974. Reference also Kriewall, T. J.: Measurement and analysis of cervical dilatation in human parturition, Doctoral theses, University of Michigan, Ann Arbor, Mich., 1974.

Ultrasonic cervimetry was introduced in the period from 1974 to 1976 by Neuman, Wolfson, and Zador. Reference Neuman, M. R. Wolfson, R. N. and Zador, I,: Ultrasonic transit time methods for monitoring the progress of obstetrical labor, *TRANSACTIONS OF PROFESSIONAL GROUP ON ULTRASONICS*—IEEE, Vol. 33, 1975; Zador, J.: Ultrasonic determination of cervical dilatation during labor, Master's thesis, Case Western Reserve University, Cleveland, Ohio, 1974; Zador, I, Neuman, M. R. and Wolfson, R. N.: Continuous monitoring of cervical dilatation during labour by ultrasonic transit-time measurement, *MED. BIOL. ENG.* 14–229, 1976; and Wallenburg, H. C. S., and Wladimiroff, J. W.: Ultrasonic measurement of cervical dilatation during labor, *AM. J. OBSTET. GYNECOL.* 126:288, 1978.

A comparison of the advantages and inconveniences of each prior art method is shown in the first four columns of the Table of FIG. 1.

2.2 Ultrasonic Cervimetry

A typical advanced method of ultrasonic cervimetry, and the analysis of the measurements obtained thereby, was expounded by Moss, P. L., et al. in the aforementioned paper Continuous cervical dilatation monitoring by ultrasonic methods during labor, appearing in *AM. J. OBSTET. GYNECOL.* 132:16, 1978.

The major goal of Moss, et al., as stated in their own words, was to evaluate ultrasonic cervimetry and to look at the characteristics of the recordings with respect to conventional variables of fetal monitoring. In particular, Moss, et al. looked at the relationship between dynamic changes in cervical dilatation and intrauterine pressure. They looked at both the amplitudes of the changes and the phase relationships between the two signals.

The installation of the transducers consisted of fixing two piezoelectric crystals, each of dimension 1 mm by 5 mm, to the external os of the uterine cervix. The installation took place at 3 cm or more of dilatation. The crystals were fixed in places dramatically opposed to each other and were so held in position by spring-loaded clips.

The ultrasonic cervimeter in use generated an ultrasound wave each second, and the total time elapsed from the emission of that signal by one crystal to the reception by the other was compiled and converted into a distance. The ultrasound wave velocity was considered to be constant at 1.48 mm per microsecond. Since time, and not intensity, of the signal was the important parameter, the crystals had to rotate more than 60 degrees from one another before an error in the measurements was introduced. Migration was not possible since the clips teeth, when closed, pierced the cervix through and through.

The dilatation value along with the fetal heart rates, the fetal electrocardiograms, and the uterine contractions were recorded on an eight channel recorder.

Clinical accuracy was 0.6 cm. When the ultrasound recording of cervical dilatation is compared to the intrauterine pressure curve, it is characterized by a baseline and wave-shape curve of dilatation (DWP). The maximal amplitude component is called cervical maximal plasticity. The onset of the DWP is related to cervical resistivity, and the end of DWP reflects the relaxation time of cervical dilatation. The data show that as dilatation enters the active phase of labor, the plasticity, the resistivity, and the duration of relaxation of the cervix increase. These observations are related to the structural changes of the cervix during labor. (*AM. J. OBSTET, GYNECOL.* 132.16 1978).

It was noted by Moss, et al. (op. cit.) that cervical dilatation and fetal descent can be monitored simultaneously by ultrasound.

2.3 Problems With Previous Cervimeters—Mechanical and Electromechanical Cervimeters The analysis of this section 2.3, and of the following sections 2.4 and 2.5, is a substantial extract and paraphrase of the aforementioned article Assessment of cervical dilatation during labor: a review, by T. van Dessel, J. H. M. Frijns, F. Th. J. G. Th. Kok, and H. C. S. Wallenburg appearing in *EUROPEAN JOURNAL OF OBSTETRICS & GYNECOLOGY AND REPRODUCTIVE BIOLOGY,* 41 (1991) 165–171.

Two main prototypes of mechanical cervimeters have been described, the calipers-type and the string-type.

In the basic calipers-type cervimeter, X-cross calipers equipped with a centimeter rule at the distal end are used to measure the distance between opposing cervical rims. The Krementsov cervimeter, called an 'orificiometer' [18], has a ring at each proximal caliper end in which the fingers of the examiner can be placed. See Krememtsov, Y. G., Improved technique for measurement of cervical dilatation, *BIOMED. ENGIN.* 1968:2:350. It enables the examiner to verify his findings by vaginal examination. The Tervila cervimeter consists of two pairs of Kelly clamps, attached separately to the cervical edges, and connected in a hinge-like way. See Tervila, L., Measurement of cervical dilatation in labour, *AM. J. OBSTET. GYNECOL.* 1953;51:374–376. The Friedman cervimeter is equipped with bulldog clips for attachment to the cervical rims. See Freidman, E. A., Cervimetry: an Objective method for the study of cervical dilatation in labor, *AM. J. OBSTET. GYNECOL.* 1956;71:1189–1193. Measurement is continuous, but readings are obtained at 2 to 10 minute intervals and plotted manually against time.

Disadvantages of these simple mechanical cervimeters are the discontinuity of readings, the lack of recording facilities and the quite heavy mechanical construction that interferes with dilatation during measurement.

In later years, low-weight calipers with cervical attachment clips were combined with potentiometers to convert the movements of the caliper arms into an electrical signal that could be recorded on a polygraph. Electromechanical cervimeters of this basic type were described by Vossius, G. in Eine Methode zur quantitativen Messung der Erweiterung und des Tiefertretens des Muttermundes Wahrend der Geburt. *Z GESAMTE EXP MED* 1961;134:506–512, by Svoboda, M. in *CSL. GYNAEKOL* 1958;23:621–623, cited by Warm R., Ueber die Messung der Muttermundseroffnung unter der Geburt. *Z ARZTL FORTBILD* 1967;61:661–666, by Richardson, J. Aa, Sutherland, I. A., Allen D. W., and Dore F., in The development of an instrument for monitoring dilatation of the cervix during labour; *BIOMED. ENGIN.* 1976;11:311–313, and by Richardson J. A., Sutherland I. A.; Measurement of cervical dilatation during labour; Physical science techniques in obstetrics and gynecology, Tunbridge Wells: Pitman Medical, Kent, United Kingdom, 1977. In the paper The electromechanical Friedman cervimeter by Friedman, E. A., and Von Micsky, L. I., an electronic cervimeter is taught as a research instrument for the study of cervical dilatation in labor. Reference *AM. J. OBSTET. GYNECOL.* 1963;87:789–792. The Freidman electronic cervimeter is attached to the cervix by a retractable row of needles. At a preset dilatation the needle attachments to the cervix are automatically released. In another instrument developed and expounded by Langreder, W. in Geburtshilfliche Messungen, *BIBL. GYNAECOL* 1965;20(S), movements are recorded by means of a photoelectric cell. The cervimeters described by Warm, R. in Ueber die Messung der Muttermundseroffnung unter der Geburt. appearing in *Z. ARTZL FORTBILD* 1967;61:661–666, and by Kazda S. Brotanek V. in Part played by cervix in uterine activity at the onset of labour appearing in *CSL. GYNAEKOL* 1962;27:333–337, have a similar design. A pair of calipers is connected to an invisible hinge in a heavy extravaginal part containing an internal potentiometer. Kazda and Brotanek report successful recordings in 90 patients without presenting data.

Siener has reported several cervimeters. The original Siener cervimeter was reported by Siener H., Ein neues elektromechanisches Wehenmessgerat zur Durchfuhrung von Kombinationsmessungen, *ARCH. GYNAKOL* 1961;196;365–372, by Siener H., First stage of labor recorded by cervical tonometry; *AM. J. OBSTET. GYNECOL.* 1963;86:303–309, by Siener H. and Wust L. Innere Wehenmessung and graphische Registrierung der Muttermunds-Eroffnung als Grundlagen zur Berechnung der Weheneffektivitat und des Weichteil-widerstandes; *GEBURTSH FRAUENHEILK* 1972;32:125–130. It was also reported by Embrey M. P. and Siener, H. Cervical tocodynamometry; *J. OBSTET. GYNAECOL. BRIT. COMMONW.* 1965;72:225–228, and in Siener H., Cervical dynamometry, a new method in obstetrical research; *AM. J. OBSTET. GYNECOL.* 1964;89:579–582. The Siener cervimeter offers the opportunity for both measurement of cervical dilatation and measurement of cervical dilatation forces, after fixation of the calipers. Later Siener used the concept of the electromechanical calipers cervimeter to construct even more sophisticated devices: the cervical dynamometer and the 'erweiterte Zervixwehenmesser' ('expanded cervix-contraction meter'). Reference Siener H., Die erweiterte Zervixwehenmessung; *GEBURTSH FRAUENHEILK* 1959;19:140–145. The cervical dynamometer allowed measurement of the pressure of the fetal head on the cervix after fixation of the intravaginal arms of the cervimeter. The 'expanded cervix-contraction meter' combined a calipers cervimeter with a metal construction for measurement of fetal descent.

The string-type cervimeter consists of strings or cords, attached to the cervix. Changes in dilatation cause changes in length of the strings which are transmitted to a kymograph by a mechanical pulley-guided system. Reference Siener H., Studien uber das Verhalten des Muttermundes wahrend der Eroffnungsperiode; *ARCH. GYNAEKOL* 1957;118:556–576. Alternatively, the changes could be electrically communicated by a linear differential transformer. Reference Smyth C. N., Measurement of the forces and strains of labour and the action of certain oxytocic drugs. Comptes Rendus du Congres International de Gynecologie et d'obstetrique, Geneva, 1954;1030–1039.

Some instruments are described for assessment of cervical properties other than dilatation. Glass and coworkers has used the medical engineering principle of indentation to design an electromechanical device for measurement of the relative softness of the cervix. Reference Glass B. L., Munger R. E., Johnson W. L.; Instrument to measure tissue softness of the uterine cervix in pregnancy; *MED. RES. ENGIN.* 1968;7:34–35. An instrument to measure the amount of pressure of the fetal head on the cervix has been reported by Noack and Blaschkowski. Reference Noack H. and Blaschkowski E., Zur Frage der graphischen Registrierung von Kontraktionen des Muttermundes unter der Geburt; *Z. GYNAKOL* 1958; 80:1609–1616.

Mechanical cervimeters are cumbersome in clinical practice and they cannot be used for continuous measurement of dilatation. Most electromechanical devices offer the possibility of continuous registration but have the disadvantage of a mechanical intravaginal part, which may interfere with cervical dilatation.

2.4 Problems With Previous Cervimeters— Electromagnetic Cervimeters

Electromagnetic cervimeters were described by Wolf in a his congress report: Wolf W., Kongressbericht. *ARCH. GYNAKOLOGIE* 1951;180:177–180; and later by Rice, D. A. in Mechanism and measurement of cervical dilatation; Doctoral dissertation. 1974, Purdue University, Lafayette, Ind. U.S.A.. With these cervimeters cervical dilatation is measured using two small induction coils, attached to opposing cervical rims. An electrical current, sent through one of the coils, establishes a magnetic field that is detected in the opposite coil and then recorded. Kriewall has used a permanent magnet dipole as a magnetic field source and two Hall-effect magnetic-field transducers as detectors. Reference Kriewall, T. J., Measurement and analysis of cervical dilatation in human parturition; Doctoral thesis, 1974, University of Michigan, Ann Arbor, Mich., U.S.A. The signals derived with this technique are processed to determine the distance between the transducers.

Electromagnetic cervimeters with clinical applicability have not been described.

2.5 Problems With Previous Cervimeters—Ultrasound Cervimeters

Abdominal routes have been used to visualize cervical dilatation by means of ultrasound during pregnancy. Reference Sarti D. A., et al. Ultrasonic visualization of a dilated cervix during pregnancy; RADIOL. 1979;130:417–420; Varma T. R., Patel R. H., and Pillai U. Ultrasonic assessment of cervix in normal pregnancy; ACTA. OBSTET. GYNECOL. SAND. 1986;65:229–233; Parulekar S. G. and Kiwi R., Dynamic incompetent cervix uteri; J. ULTRASOUND MED. 1988;7:481–485.

Vaginal routes have been used to visualize cervical dilatation by means of ultrasound during pregnancy. Reference Balde M. D., Stolz W., Unteregger B., and Bastert G.; L'echographie transvaginale, un rapport dans le diagnotic de la beance du col uterin; J. GYNECOL. OBSTET. BIOL. REPROD. (Paris) 1988;17:629–633.

Transperineal routes have been used to visualize cervical dilatation by means of ultrasound during pregnancy. Reference Lewin B., L'echotomographie perineale. Une nouvelle methode de mesure objective du col; J. GYNECOL. OBSTET. REPROD. 1976;5:289–295; and Jeanty P., Perineal scanning; AM. J. PERINATOL. 1=86;3:289–295.

Reports in the literature dealing with systematic visual assessment of cervical dilatation during labor could not be found by T. van Dessel, et al. (op. cit.), nor by Applicants.

A different approach uses two ultrasound transducers attached to opposing rims of the cervix. An ultrasonic signal generated by one transducer is received by the opposing one. Since the ultrasound velocity is known, the transmission time allows computation of the distance between the transducers.

The first ultrasound cervimeter was described by Zador et al. in 1974. Reference Zador, I, Neuman, M. R., and Wolfson, R. N.; Continuous monitoring of cervical dilatation during labour by ultrasonic transmit-time measurement; MED. BIOL. ENGIN. 1976;14:299–305; also Zador, I., Wolfson R. N., and Neuman, M. R., Ultrasonic measurement of cervical dilatation during labor; ANN. CONF. ENGIN. MED. BIOL. 1974;16:187. These authors used spring-loaded clips to attach the transducers to the cervix. A total of 24 readings of women in labor were reported, but no specific data were given. Apparently, practical problems were encountered, because further clinical studies with this device could not be found.

A similar cervimeter has been presented by Kok, et al. in 1976 in preliminary reports. Reference Kok, F. T., Wallenburg, H. C., and Wladimiroff, J. W., Ultrasonic measurement of cervical dilatation during labor; AM. J. OBSTET. GYNECOL. 1976;126:288–290; also Eijskoot, F., Storm, J., Kok, F. T., Wallenburg, H., and Wladimiroff, J.; An ultrasonic device for continuous measurement of cervical dilatation during labor; ULTRASONICS 1977;55:183–185. The problems with the fixation of the transducers to the cervix were eliminated by using special spiral-shaped transducers. The data was analyzed off-line by a computer, and accuracy and precision in vitro and in vivo were shown to be good in a well-documented study of 62 women in labor. Reference Kok, F. T., JGT; Ultrasonic cervimetry (summary in English); PhD-Thesis, Erasmus University, School of Medicine and Health Sciences, Rotterdam, 1977.

Cervical dilatation appeared to follow a wave pattern reflecting the intrauterine pressure curve. Maximal cervical dilatation coincided with the maximal intensity of each contraction. Generally, the derived curve of cervical dilatation showed the sigmoid shape postulated by Friedman (op. cit.) and by Krementsov Y. G. in Improved technique for measurement of cervical dilatation; BIOMED. ENGIN. 1968;2:350. A decelerative phrase was never detected. Using a similar device Moss and coworkers have investigated 13 women in labor. Reference Moss P. L., Lauron P., Roux J. F., Neuman M. R., and Dmytrus K. C.; Continuous cervical dilatation monitoring by ultrasonic methods during labor; AM. J. OBSTET. GYNECOL. 1978;132:16–19. T. Van Dessel, et al. (op. cit.) observed—contrary to the findings reported by Kok, Zador I, Neuman M. R., Wolfson R. N. in Continuous monitoring of cervical dilatation during labour by ultrasonic transmit-time measurement. MED. BIOL. ENGIN. 1976;14:299–305—that the peaks of uterine contraction and cervical dilatation were out of phase.

Ultrasound visualization of the cervix may be helpful in monitoring the patient at risk for premature delivery, but does not allow continuous registration of dilatation during labor. However, ultrasonic cervimetry does offer continuous and reliable recording with little discomfort to the patient, but clinical data has been limited. T. van Dessel, et al., (op. cit.) felt in 1991 that "[u]ltrasound cervimetry may be a useful research tool for the study of the cervical response to the uterine contractions during labor. For clinical obstetric purposes, however, digital assessment of cervical dilatation seems sufficient."

2.6 Problems With Previous Ultrasonic Cervimeters—Position-holding of Placed Probes In the predecessor patent application it is taught that ultrasonic transducers to which various barbs of the order of corkscrews to fish hooks are affixed may be reliably semi-permanently affixed to the cervix os, which is devoid of nerve endings. The fact that the placement of these vicious-looking devices may benefit the patient without inducing pain or harm—much in the manner of the similarly-appearing corkscrew probe of a cardiac pacemaker—does little to assuage the sensitivities of the female in whose birth canal these devices are to be affixed.

Especially since the ultrasonic probes are generally to be maintained in position for intervals ranging from days to weeks, and for total observational periods ranging to several months, while the carrier female is conscious, and because the carrier female must be able to recognize a probe should it come loose and become resident in, or become ejected from the vaginal canal, the patient should be shown the probe and its affixation means, and its function and operation should be both explained to the patient and understood by the patient.

The present invention will be seen to be directed to a more psychologically-user-friendly placement and holding device for cervical instrumentation, including a device for holding pair of ultrasonic transducer probes as may be used with a cervical dilatation and effacement monitor.

2.7 The Desirability of Continuous Accurate Convenient Cervical Dilation/effacement Monitoring, With Automated Alarms The inventors of the present invention are of a contrary opinion to the opinion of T. van Dessel, et al., (op. cit.) in the aforementioned paper that "digital assessment of cervical dilatation . . . [is] sufficient" and that, by implication, ultrasound cervimetry has no role in the clinical environment.

In the first place, the only realistic alternative to ultrasonic cervimetry is, and has proven to be, no cervimetry at all, and exclusive reliance the time-honored approach of digital assessment of cervical dilatation. This procedure, which should be, and regularly is, performed every hour after the onset of labor, is (i) manifestly inadequate to detect the onset of labor itself, (ii) laborious, (iii) without automatic contemporaneous generation of a permanent record, and (iv) of no greater quality in results obtained than the skill and attentiveness of the practitioner.

Despite the lack of clinical, or patient portable, instrumentation for the detection of the onset of labor (should such event be sharply definable, and it is), the detection of this event is very important in those rare cases where premature labor must be avoided. The inventors of the present invention are involved in the verification of instrument with one of the major centers for the management of problem pregnancies and premature births in the United States if not also the world circa 1994. Prolongation of gestation beyond a certain, threshold, number of weeks is currently very, even crucially, important to the survival of the fetus at birth. This minimum gestation period for live birth has greatly decreased in recent years, but cannot be expected to decrease to shorter than the period within which spontaneous abortions, or premature labor, occur in the human female. Accordingly, the only way that some fetuses will ultimately be viable is if tenure in the womb is prolonged.

Powerful drugs exist to arrest labor. However, these drugs cannot be continuously, or even regularly administered, during the projected terminal phase (at whatsoever period gestation) of a particular problem pregnancy. Accordingly, it is of crucial importance to detect the onset of labor (should such event be detectable, and it is) at the earliest possible moment in order that it may be stopped, if desired or required, by the administration of drugs or otherwise.

Next, once labor has begun, and even in normal pregnancies and deliveries, the inventors of the present invention do not take such a cavalier attitude as do their peers to the present lack of hard, recorded, and/or instantaneous quantitative data about what has gone on, and is going on, from moment to moment during labor. The dilatation/effacement of the cervix is a very good indicator of the progress, and or of problems, with labor.

2.7.1 Timing of Therapeutic Regimens Based in Cervical Dilation/Effacement Monitoring, and Problems with the Timely Administration of Same The first, and potentially greatest, advantage to the continuous monitoring of cervical dilatation/effacement during labor, if not also in the period before, is that it can promote superior timing in the administration of medical therapies to support the suppression of labor or during labor. Cervical dilatation/effacement monitoring promotes the timely and optimally timed therapeutic administrations in consideration of (i) the earliest possibly recognition of changing conditions, including problem conditions, during labor, (ii) a definitive record of exactly how long certain conditions have persisted, and (iii) the possibility of machine aids, ranging from alarms to the comparison of profiles to mathematical modeling.

In short, the fact that most births occur normally even should the midwife or obstetrician be ignorant of cervical dilatation, and the complementary fact that some births encounter problems, are both facts of nature, and not of man. However, the fact that intervention in the birth process, primarily by Caesarian section, is occasionally ancient and generally successful does not invariably mean that it has been optimally timed for the health of the fetus and/or the mother.

Timing in the administration of therapeutic regimens during labor has always been recognized to be an issue. For example, the administration of pain-killing drugs to the mother is permissible during the early stages of labor whereas the administration of the same drugs becomes impermissible in later stages of labor. For example, a Caesarian delivery is not normally attempted until some lapse of reasonable progress towards a normal, vaginal, delivery. The questions that should be asked by a clinical practitioner in considering the efficacy of a monitor device in accordance with the present invention are these: Is there any evidence that the timing of some (or any) interventions is more critical than the timing of other interventions, or more critical than is generally recognized, or, God forbid, more critical that is generally possible under current methods for the measurement of the progress of labor? If so, what interventions would so benefit? Finally, is the monitoring of cervical dilatation and/or effacement (the thinning of the cervical rim, which thinning is of course proportional to the expansion of the cervix) an appropriate, or useful, measure of the progress, and/or the onset of problems, during labor? The present specification does not contain proof that the answers to the first and the third questions are yes, nor need it do so. However, data from animal trials at the Fetal Treatment Center of the University of California, San Francisco, during 1994–1995 suggests that this "yes" answer.

Also discerned in the animal trials, which confirms the experience of most obstetricians, is the very great utility of timeliness in the administration of tocolytic drugs to prevent premature labor. Labor induces physicochemical changes in the woman's body. The pharmacology of tocolytic drugs is believed to counteract, or oppose, these changes, thereby stopping the progression of labor (with sufficient dosage). However, and as every mother knows, labor is progressive. Once the woman's body is fully involved it is simply not possible to reverse the course of labor with drugs, and to attempt to do so might be dangerous.

Because the course of labor in each woman is different, it is hard to make complete generalizations about the efficacy of timeliness in the administration of tocolytic drugs. Generally, however, the clinical experience of the two clinician inventors of the present application at the Fetal Treatment Center of the University of California, San Francisco, leads to the following statement. First, if it is absolutely certain that childbirth is desired to be postponed (which it usually is if the attending physician is even thinking about the possibility), then it cannot be said that any administration of tocolytic drugs after the onset of true labor is unambiguously detected is "too soon". Indeed, the tocolytic drugs would desirably be given instantaneously after the onset of labor is confirmed.

At this earliest time a baseline dosage of a tocolytic drug will be sufficient to arrest labor in such a percentage of women (other pathological conditions not prevailing) as is currently un-quantified, but that is very, very roughly estimated to be about 60%. After injection of an initial bolus, the dosage is normally continued at a lower rate, depending upon the woman's condition and other indices of the progress of labor. This is the most optimal regimen presently known. Increasing the dosage is unavailing, and likely dangerous. Even with the best drugs and regimens presently known, arresting labor at this point is troublesome, and the those drugs and dosages commonly believed appropriate and sufficient by a skilled specialist attending physician/ obstetrician will not suffice to successfully arrest labor in, very roughly, about 40% of the time. Finally, after a woman has been in full labor for only a few hours, it is generally unavailing either to commence, or to continue, any drug regimen at all to try and arrest labor. Any drugs sufficient to do so after a certain point would likely be dangerous to the mother and/or fetus.

In certain "high-risk" pregnancies the expectant mothers are hospitalized during a certain, critical, portion of the pregnancy typically from twenty-four (24), or less, to thirty-two, or more, weeks. The forced inactivity of the mother contributes to the avoidance of premature labor. However, even some percentage of these expectant mothers will, often for unexplained reasons, experience the onset of labor. The hospital environment then becomes very useful for the relatively immediate obtaining of medical advice, and care including the early infusion of a tocolytic drug. These prolonged hospital stays of a generally otherwise healthy patient, or at least a patient sufficiently healthy so as not to otherwise warrant hospitalization, is extremely expensive in the U.S. circa 1995. It is hard to tell when such an extreme preventive measure is warranted, and when it may, in subsequent pregnancies of a high-risk woman, again become warranted. One time-honored technique is, quite unfortunately, to let a woman accumulate such a series of spontaneous abortions and non-viable premature deliveries as ultimately appear to require hospitalization if any viable live birth is to be realized.

There in an additional, prevalent but somewhat unpredictable, problem occurring with premature delivery/ spontaneous abortion of pregnant women suffering trauma, including the trauma of being operated on themselves for conditions that may or may not concern their pregnancy, or having their fetus operated on in the womb. These women are much more likely than normal to experience spontaneous abortions and non-viable premature deliveries. However, the timing of these occurrences is unpredictable. Hospitalization of every woman experiencing a fall or other untoward event during pregnancy could would be exceedingly expensive, and disruptive.

The previous discussion "boils down" to the facts that childbirth has never been without risk for either the child or the mother, and that some premature infants are stillborn or handicapped, sometimes exceedingly severely so. It has been so since the human race began. However, it may not be cost effective to "procreate by the percentages" in a modern industrialized society. If people are to have fewer children, as population trends both domestically and worldwide seem to necessitate, than more becomes invested not just in each living child but in each opportunity to have a living, healthy child. With the continuing deferral of the age of childbearing first by American women of the "baby boomer" generation, and now by their career-minded daughters, many American women are undertaking to have children at chronological ages where their probability of reproductive success is diminished simultaneously that the remaining years during which birth can be given are waning. Some cost-effective means of improving the likelihood of realizing satisfactory full-term pregnancies for these women would be highly desirable.

The present invention does not directly concern the medical diagnosis of problems during delivery, which is part of the evolving medical art of obstetrics. The present invention does concern, however, new machines and methods for both the comprehensive measurement and display of, and the generation of alarms and infusion of tocolytic drugs responsively to, the measurement of cervical dilatation/effacement during labor. The present invention will be seen to concern a new approach to attempting to maintain a fetus in the womb for such a minimal gestation period as is highly beneficial to the fetus, highly salubrious to the mental health and well being of the parent(s), and high cost effective to society.

2.7.2 The Communication of the History of a Birth Based in Cervical Dilation/Effacement Monitoring The oral record and the written does not suffice for the communication of the stages, and circumstances, of complicated labor. The hard-copy, graphical, record of a continuous monitoring of cervical dilatation/effacement during labor can promote a number of ends. It permits the ready visualization of the progress of the labor. It permits all temporal junctures at which therapies were administered to be identified, and the results of these therapies (insofar as affecting cervical dilatation/effacement) recognized. It permits the ready communication of a history of the labor to (i) students, (ii) history, (iii) medical review boards and courts, and (iv) other physicians, including those who may attend other labors of the same female some years hence.

2.7.3 Previous Monitoring of At-Risk Pregnancies

A previous attempt to monitor pregnancies at risk of early delivery relied on strain gauges held in contact with the abdomen to detect premature uterine activity. A monitoring device so operating has been made and sold by Tocos, Incorporated of Orange County, California and also by HealthDyne. The device is typically used to sample uterine activity only some few hours a day while the woman patient is hooked up to a monitor. The monitor transmits the sensed uterine activity and movement via modem to a regional office for assessment by a nurse. If excessive activity is detected then the woman will be directed to contact her physician.

The utility of this system in registering the onset of true labor, even during such periods as the system is connected and operating, has been questioned in the ob-gyn literature. The system suffers from sensing and reporting normal uterine contractions which may not be true precursors, or the best indicators, of the actual onset of labor. A physician will, as previously explained, also assess cervical dilatation/effacement, as well as uterine contractions, in determining whether labor is occurring.

2.7.4 Diligence in Childbirth Monitoring Based in the Monitoring of Cervical Dilation/Effacement Childbirth in humans is a lengthy process which can commence totally asynchronously with the other duties and schedule of an attending obstetrician or midwife. The attentiveness of personnel attending to the labor can sometimes languish over the long periods involved. It is equally as undesirable that these personnel should be overly zealous. It is (i) difficult, (ii) unreasonable on the basis of medical results obtained, (iii) and more disturbing than beneficial to the patient, that a physician or attending midwife should be making excessively frequent manual digital assessment of the dilatation of the cervix during labor.

Accordingly, manual assessment of cervical dilatation during labor that is either too infrequent, or too frequent, is avoided. However, there is a fair amount going on in the cervical dilatation on a time scale that is short, and thus insufficiently captured, relative to even the most frequent manual digital assessment. Namely, this dilatation is cyclic on a time scale of typically from one (1) to two (2) minutes, as will be shown in this specification. Moreover, there is no desire to delay the recognition of changes, especially such changes as may be significant, simply because they do not coincide with the periodic, and likely infrequent, schedule of manual digital assessment.

In most labors and deliveries, including those that have problems, observational vagaries as may result in (i) imprecision and/or (ii) untimeliness in detection/measurement of the dilatation/effacement of the cervix the are of no consequence. The challenge is with those few difficult, often premature, labors and deliveries in which the timeliness and quality of information may be, or become, critical. In episodes of labor of this sort the physician faces a dilemma. His continuing observational interventions may precipitate the very events that he/she seeks to avoid. Conversely, optimal intervention may be compromised if the physician is not in possession of the most timely and accurate information.

Accordingly, a system that would continuously, accurately and reliably monitor cervical dilatation/effacement during labor without substantial discomfort, inconvenience, disturbance or hazard to the patient would be very desirable. It would be even better if such a system were usable outside a hospital, or clinical, environment. Finally, it would be very useful if such a system could be proactive, or at least timely reactive, to prevent premature labor/spontaneous abortion. The present invention concerns such a system.

SUMMARY OF THE INVENTION

The present invention contemplates infusing of tocolytic (labor-preventing) drugs in response to the onset of premature labor or spontaneous abortion as is detected by ultrasonic monitoring of the dilatation and/or effacement of the cervix os.

The purpose of the invention is to avoid spontaneous abortion (death of the fetus), and/or to postpone labor until the fetus is more likely to be born alive, less likely to suffer the deleterious health effects of premature birth, and less likely to require the extensive postnatal care that is, circa 1995, occasionally extremely expensive (ranging to $1M+ U.S. circa 1995) for infants born viable but prior to thirty-two (32) weeks gestation.

In one embodiment of the present invention, the onset of labor of a pregnant human female is continuously automatically monitored, potentially for periods of several months, by ultrasonic measurement of the dilatation and/or effacement of the cervix os. The preferred measurement is of both the (i) absolute dilatation and/or effacement (i.e., an absolute dimension), and also the (ii) cyclical variations in dilatation and/or effacement (i.e., relative changes in a dimension) of the cervix os. The measurement is preferably performed with and by a real-time transit-time ultrasonic monitor, and more preferably by a computerized ambulatory monitor. The monitor is coupled to ultrasonic transducer probes that are preferably emplaced, and held, in the vaginal canal in preferred positions about, and across, the cervix os.

Upon detection of certain conditions in the dilatation or, equivalently, the effacement of the cervix os such as are indicative of the early onset of labor (equivalently, sponta- neous abortion), time is of the essence if the onset of full blown labor and ultimate birth/abortion is to be avoided. Two transducer probes of an ultrasonic monitor are affixed at, and about, the cervix os in a first placement opposed across the cervical opening if dilatation is to be measured, and in a second placement upon the wall of the cervix os if effacement is to be measured. The initial physical placement of the transducer probes upon the cervix os of a particular woman determines the absolute, baseline, dimensional measurements. Baseline cervical dilatation and effacement are each typically less than one (1) centimeter, and may even be nearly zero if the two probes are nearly touching.

The conditions that are preferably detected by the ultrasonic cervical monitor may be any one or ones of (i) absolute cervical dilatation, with an alarm threshold limit of typically greater than a preset increment of one to two (1–2) centimeters over the baseline measurement, (ii) absolute cervical effacement, with an alarm threshold limit of preferably one to two (1–2) centimeters over the baseline measurement, and/or (iii) greater than a present, normally 10%, cyclic dimensional variation in either dilatation or effacement within an alarm threshold preset limit of a fixed number, preferably less than five (5), cycles per hour.

Preferably both (i) the absolute dimensions of cervical dilatation or effacement, and also (ii) cyclical variations in such dilatation or effacement, are detected. The preferred monitor is self-normalizing to the baseline measurements. The threshold value(s) associated with each condition is (are) preferably variably preset, normally in a simple programming operation performed by the woman's obstetrician. The monitor is also possessed of manufacturer's default presets, and it will assess any programmed preset for being reasonable, and within a manufacturer's allowable dimensional range (as reflects the anatomy of a human female).

In response to detection that any one or ones of variously predetermined cervical conditions—and preferably both of the preferred two monitored conditions of (i) absolute dilatation/effacement and (ii) detected cyclical variations in measured dilatation/effacement—have exceeded an associated preset threshold(s), the preferred system of the invention preferably first produces an alarm, preferably an audible alarm. The preferred audible alarm is reasonably dignified, and is of the order of the only-modestly-obtrusive volume and tone of a common telecommunications pager. The female patient has normally been instructed in advance to respond to the alarm by doing what she can to cease such behaviors as may be inducing the commencement of labor, by becoming inactive and preferably assuming a supine position, and/or by immediately contacting her obstetrician/gynecologist by telephone (preferably by cellular telephone carried by the patient in geographic areas so served).

Nonetheless to the patient female's best efforts, and/or professional medical advice timely forthcoming in real time, labor may often continue. In this eventuality—or occasionally if so predetermined by programmed entry, immediately upon occurrence of the alarm condition (regardless of whether or not an alarm is sounded)—the preferred system of the invention will cause an infusion of a predetermined dosage of a tocolytic (labor-preventing) drug. The administration of the drug is preferably subcutaneously by an ambulatory infusion pump electrically triggered and controlled by the cervimeter monitor. The infusion pump may be powered by compressed gas, normally nitrogen, or by electricity, normally in the form of batteries. If electrical, the pump may use a motorized pump, including motors of the solenoid type and pumps of the peristaltic type. The preferred infusion pump has the extensive programmable controllability and alarms as to its performance (integrated with the alarms of the monitor) as are typical, for example, of the existing MiniMed® 404-SP ambulatory miniaturized battery-powered infusion pump of MiniMed Technologies (MiniMed® is a registered trademark of MiniMed Technologies).

The monitoring, and potential infusion, preferably transpires between 28 and 34 weeks of pregnancy. The preferred (and also the default) three threshold condition(s) preset in the monitor, and also alarmed by the monitor if exceeded (in combination), are: (i) more than one (1) centimeter of cervical effacement above baseline, or (ii) more than one (1) centimeter of cervical dilatation above baseline, coupled with (iii) more than five (5) cycles of greater than ten percent (10%) in effacement or in dilatation in the course of any one (1) hour period. For example, six (6) cycles of twenty percent (20%) variation in dilatation without accompanying increase in dilatation of more than one (1) centimeter will not suffice to cause an alarm. The physiological interpretation of such an occurrence would be that the woman is experiencing uterine (and cervical) contractions, but is not (yet) entering labor. Conversely, the same cyclical contractions, and corresponding cyclical variations in dilatation/effacement, further accompanied by a one (1) centimeter expansion of the dilatation of the cervix os would be indicative of early labor, and would be alarmed by the monitor.

The woman wearing the ambulatory monitor and infusion pump is given the ability to turn off the alarm. She is also accorded a variably preset short period of time, normally five minutes, in which to reject, or suspend action on, those indications of cervical condition that are commonly displayed on the monitor, and/or the interpretation of the onset of labor that has just been made by the monitor from these indications. If the woman does not suspend action, the monitor will trigger the infusion pump to automatically subcutaneously inject a tocolytic drug. This injection is neither so large nor sensation-inducing so as would physically disrupt and affect the woman regardless of her present posture and/or activity such as, for example, driving a car. There is, however, a feeling, and a possible psychological impact, to the injection. The woman is accordingly permitted to suspend, or to permanently override, the impending injection while she momentarily prepares herself, and/or contacts her physician-obstetrician by telephone. If the woman and/or the physician decide, a pushbutton activation of the monitor can cause the tocolytic drug to be summarily injected.

The presently preferred tocolytic drugs are Terbutaline and Ritodrine, and more preferably Terbutaline. The preferred profusion pump preferably contains 0.5 cc of a 1 mg/cc sterile solution of Terbutaline. The Terbutaline is preferably infused subcutaneously almost immediately that the compound threshold conditions indicating onset of labor are sensed, preferably as a bolus in the amount of 0.25 mg of (0.25 cc of the 1 mg/cc solution). Infusion thereafter desirably continues at the rate of 0.2 mg per hour (0.1 cc of the 1 mg/cc solution) until, if medical aid is not earlier obtained, the supply of the drug is exhausted after approximately another 7.5 hours, or else the patient is directed to disconnect the infusion line or pump.

The system is fail safe in design, and will not harm the patient even if all the Terbutaline is instantaneously injected. All normal failure modes—especially as are attendant upon loss of battery or pressurized gas power, or physical disconnection of any of the ultrasonic transducers, monitor and infusion pump, or infusion catheter—will cause that no drug will be infused.

The system of the present invention is also useful in more routine, full term, pregnancies and labor. The monitor and its probes in combination with the controlled infusion pump may be fitted, for example, to a woman entering a hospital at full term of pregnancy in the first stages of labor. The monitor may be flexibly programmed to, for example, continuously or periodically or occasionally infuse a tocolytic drug in order to "even out" the progress of labor, and/or to postpone labor some hours in order that the actual childbirth may transpire at a time most safe for the mother and her newborn child (normally in the morning), and convenient to the attending hospital staff and physician.

In these manners of using the monitoring and infusion system of the present invention, the onset of labor/spontaneous abortion can be (i) early detected, (ii) early alarmed and (iii) early beneficially altered even before it is possible to receive the diagnosis or treatment of a physician or other health care provider.

These and other aspects and attributes of the present invention will become increasingly clear upon reference to the following drawings and accompanying specification.

BRIEF DESCRIPTION OF THE DRAWINGS

FIG. 1 contains a table comparing the advantages and inconveniences of prior art methods of cervimetry with the method, and cervical monitor instrument, of the system of the present invention.

FIG. 5a is a graph showing a calibration of the ambulatory cervical effacement/dilatation monitor used in the system in accordance with the present invention.

FIG. 5b is a graph showing the typically varying dilatation of the cervix uteri of a human female, or any higher primate, during labor.

DESCRIPTION OF THE PREFERRED EMBODIMENT

Figure 2:
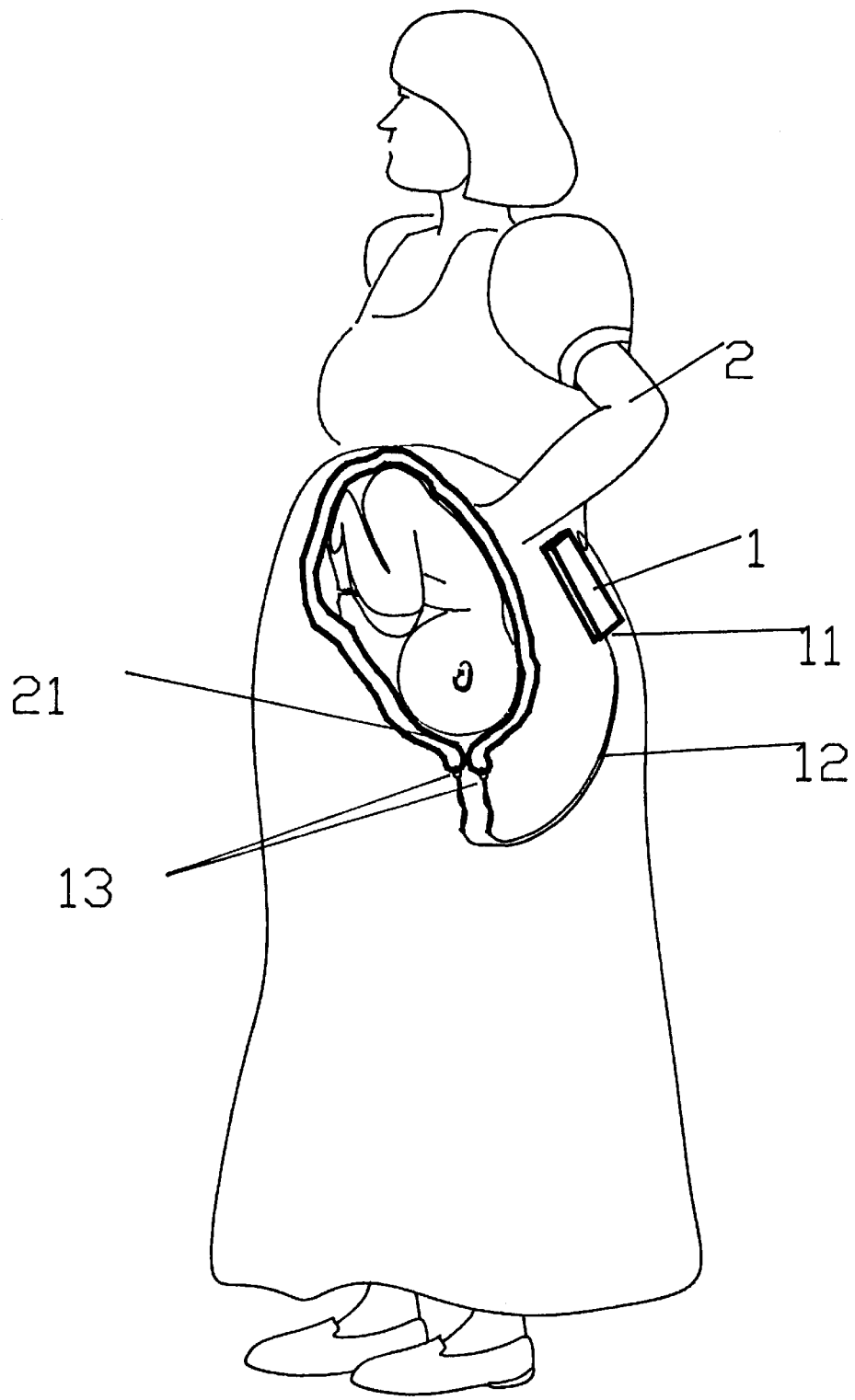
FIG. 2 is a diagrammatic perspective view showing a preferred embodiment of a preferred system in accordance with the present invention including both an ambulatory cervical effacement/dilatation monitor having disposable probes, and an ambulatory infusion pump, in operational use for monitoring, and for infusing upon the occurrence of certain conditions, an ambulatory pregnant human female.

The present invention includes both a (i) monitor of cervical dilatation or, alternatively, effacement, in combination with (ii) an infusion pump. The monitoring is directed to detecting and measuring the dilatation—meaning the opening—or, equivalently, the effacement—meaning the thickness of the rim—of the cervix uteri, of the cervix os of a human female particularly so as to detect the onset of labor.

It should be noted that as the cervix expands during labor, increasing the dilatation distance, the rim of the cervix stretches and becomes thinner, decreasing the effacement distance, or thickness of the rim. One phenomena is related to the other. Both phenomena show the same cyclical variation during labor, and each may be correlated to the other.

The probes of an ultrasonic acoustic cervimeter that is a part of the system of the present invention are preferably affixed across the major chord, or diameter, of the cervix uteri from a one side to the other, or at least across a minor chord for such a maximum distance of separation on the face of the cervix as is possible. In such positions the probes measure dilatation.

However, the probes may be affixed, if required or desired, along but a single radii of the cervix with a one probe located more centrally, on an interior wall of the cervix (which is in the overall shape of a torus) and with the remaining probe located nearby on the exterior wall of the cervix. In such a position the probes measure effacement.

The cervical monitor of the system of the present invention may be implemented in many different forms—ranging from a straightforward ultrasonic acoustic distance measuring device, or sonic cervimeter, to a full-blown computerized cervical dilatation/effacement alarming monitor with a memory and a time-based display of a running history of dilatation/effacement measurements. One preferred embodiment is as a battery-powered monitor with a memory and a graphical display, plus combined audible and visual alarm indications, that is completely self-contained and portable, and that is intended for continuous use on, partially within, and by, an ambulatory female patient.

This embodiment typically takes one hundred (100) measurements a second, forming a running average of the cumulative measurements taken over a period of five (5) seconds and displaying the averaged measurements for the previous one hundred and twenty-eight (128) five-second intervals (for a total of 10⅔ minutes). The cumulative measurements for a longer period are stored to the capacity of memory, typically the averaged measurements for at least the previous six hundred and forty (640) five-second intervals for a total of over sixty (60) minutes). The ambulatory monitor typically so functions on two (2) 9 v.d.c. dry cell batteries, typically for a period of more than eight weeks.

A table comparing the major advantages and inconveniences of prior art methods of cervimetry with the method, and the cervimeter, of the system of the present invention is shown in FIG. 1. It may immediately be observed that the ultrasonic cervimetry method, nonetheless to being performed by an instrument that is uniquely compact and suitable for ambulatory use, to record a history of cervical dilatation/effacement that is described as "total" as opposed to "limited". By this it is meant that previous monitors, especially including ultrasound monitors, recorded a history of cervical dilatation/effacement only when the patient was "hooked up" to the previous monitors, usually in a hospital after the onset of labor. Data regarding any such long or short term transient events during pregnancy as did not lead to the full onset of labor was unrecorded and unavailable. Indeed, very little is known at the present time about exactly what (other than the lapse of time, or intentionally-administered medications) will most likely induce the onset of labor in a particular human female, and what precursors to this event and/or flags to the likely causative agent(s) (such as exercise, or diet, or temperature) might be observed. The preferred cervical monitor is, of course, dedicated to providing a full and complete record of cervical dilatation/ effacement over a period potentially as long as many months. During this period of time there is little or nothing regarding the dilatation (or, equivalently, the effacement) of the cervix that will not be recorded, and archived into a history store that is retrievable to and analyzable by, a health care professional. Accordingly, the recorded history is described as "total".

Because the preferred cervical monitor is intended to be in continuous use twenty-four hours a day during all periods—which periods may be protracted and many months in duration—when the dilatation (or, equivalently, the effacement) of the cervix of the female patient wearing the monitor is of medical interest, it is possible for the monitor to make a visual or audible alarm, as well as to control the administration of tocolytic drugs, when certain conditions are detected. Certain basic conditions regarding the cervical dilatation/effacement curing the onset of, and during the progress of, labor are well understood, and the monitor looks for, and alarms, the occurrence of these conditions.

It may well be, and is expected, however, that certain high-risk pregnancies will exhibit detectable, possibly unique, phenomena prior to events such as spontaneous abortion. If particular warning signs to the continuation of the pregnancy of a particular human female, or class of human females, can be recognized from the study of historical data on such female, or on such class of females, then it is contemplated that it will be desirable to warn such a female or females of the incipient occurrences of such signs in her/their later pregnancies. As will be seen, the preferred ambulatory cervical monitor is a programmable device. If necessary or desired, it can be preset to alarm, and to variously alarm, conditional upon almost any condition(s) of the cervix transpiring over almost any time interval(s) that the monitor is capable of detecting. Although setting up the preferred ambulatory cervical monitor to alarm upon arbitrarily determined criteria (one, or many) involves (by present understanding of cervical dilatation/effacement indications in high-risk pregnancies) highly skilled labor and attendant expense, it should be understood that the monitor is intended to be used, among other applications, on pregnant females that have never successfully carried so long so as to give live birth, let alone to term. Moreover, it should be understood that if cautions performed by the female and/or her medical advisors in response to monitor alarms and/or recorded records can prevent, or can even slightly delay by a matter of months or even scant weeks, highly premature births, then the very considerable expense of administering to premature newborns can be ameliorated, or even substantially saved.

This simple concept deserves further exposition. People do not like to, and effectively cannot, be told that they cannot have children because they are at risk of giving birth prematurely, and at great expense. People, especially those who desire but do not yet have children, do not like to think that such medical care, no matter how expensive, as might permit their prematurely born child to survive is being withheld on economic grounds. An ounce of prevention is worth a pound of cure—although it is perhaps not so "showy" in terms of hospital obstetrics facility, practice, and practitioners. A successful obstetrician in the current U.S. health care environment (circa 1995) is one who judiciously avoids problems, not just one who is skilled in overcoming problems. The monitor and the entire system of the present invention are directed to aiding an obstetrician, a general health care practitioner, and a woman patient herself, in avoiding the expense, risk, and potentially traumatic consequences of premature birth.

A diagrammatic perspective view of a preferred embodiment of the system of the present invention is shown in FIG. 2. An ambulatory cervical effacement/dilatation monitor 1 having disposable probes 13 is in use for monitoring a pregnant human female 2 (shown partially in cut-away view and partially in phantom line) is shown in FIG. 2. The female 2 is ambulatory. Wires 12 connect a portable control unit 11 to the probes 13, The wires 12 descend (in the standing female) from the cervix os 21 whereat the probes 13 are affixed through the vaginal canal (not shown) to the exterior of the body of the female 2. They then proceed past normal boundaries and apertures of both underclothing and clothing to the site of the control unit 11, which may be worn virtually anywhere on the body in a position covered or uncovered by clothing as is desired. The wires 12 are normally quite small and flexible, and are appropriately sheathed in soft and flexible plastic. The preferred surrounding plastic is preferably (i) surgical grade, (ii) antibacterial, (iii) and readily cleansed. The entire interconnection system of the wires 12 is designed with due consideration to (i) comfort for long term wear, and (ii) avoidance of establishing any path by which germs might abnormally be conducted to the region of surface of the cervix 21. Both the wires and the preferred ultrasonic transducers are coated with a biologically inert material, preferably respectively Teflon® polymeric material Teflon is a registered trademark of E. I. DuPont de Nemours) and EPO-TEK™ coating (EPO-TEK is a trademark of Epoxy Technology, Inc.).

The ambulatory cervical effacement/dilatation monitor 1 having disposable probes is connected to an ambulatory infusion pump 3. The infusion pump contains a reservoir containing a tocolytic drug (not shown). The infusion pump and its reservoir are flow connected by a catheter 31 to a needle (not shown in FIG. 1, shown in FIG. 7b) held under a cuff 32 for the purpose of making a subcutaneous injection of the tocolytic drug under automated control of the monitor 1.

Figure 3A:
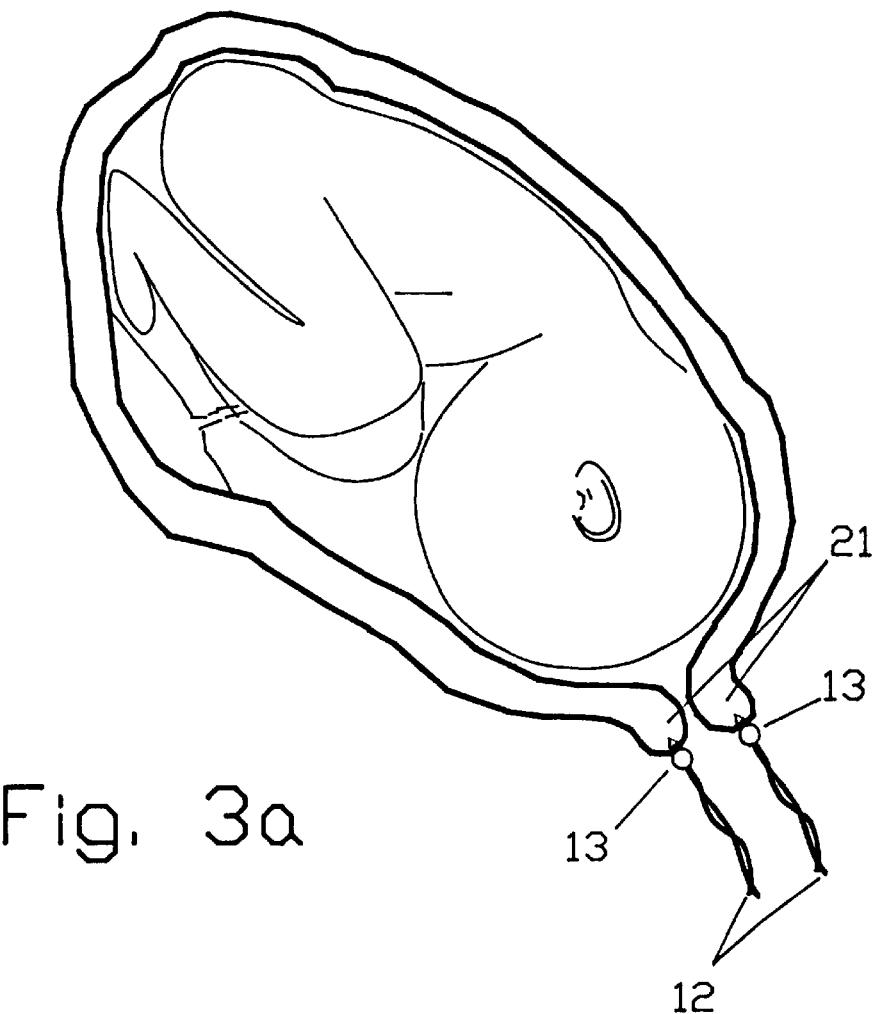
FIG. 3a is a detail diagram of first positions of affixation of the disposable probes of the ambulatory cervical effacement/dilatation monitor to the cervix uteri of the ambulatory pregnant human female previously seen in FIG. 2, the first affixation positions being so as to monitor cervical dilatation.

A detail diagram of the affixation of the disposable probes 13 of the preferred ambulatory cervical effacement/dilatation monitor 1 to the cervix os 21 of the pregnant human female 2 (previously seen in FIG. 1) is shown in FIG. 3. The particular affixation of the probes 13 that is illustrated is where each of the two probes is on the rim of the cervix 21 at roughly 180° separation. In this position the probes 13 are positioned to measure, by the delay in an ultrasound pulse traveling between them, the cervical dilatation, or distance across the cervix. Note that in the FIG. 3 it appears as if the central opening of the cervix os is void and filled with air, which would be unsuitable to transmit ultrasound. In actual fact the complete path in a substantially straight line between probes 13 is completely filled with tissues, mucous and fluids. An ultrasonic path can be reliably established and maintained between the probes 13 under all normal and abnormal conditions. Indeed, neither ultrasonic signal attenuation nor change in attenuation (signal level) presents any significant problem(s) or challenge(s)—at least when the preferred probes are used (as will be discussed in conjunction with FIG. 4)—and there is little difficulty that (i) and ultrasonic pulse emitted at a one of the probes 13 will be duly received and the other one of the probes 13, and that (ii) this pulse will travel a true path, meaning straight between the two probes 13.

Figure 3B:
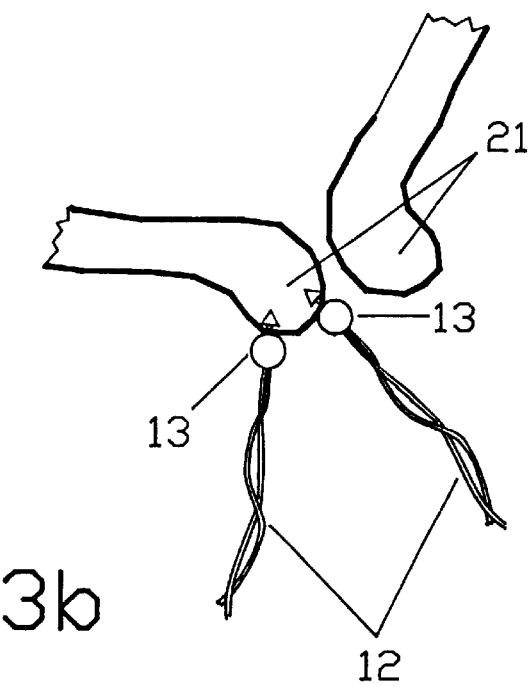
FIG. 3b is diagram, at an enlarged scale from FIG. 3b, of a second positions of affixation of the disposable probes to the cervix uteri of the pregnant human female previously seen in FIG. 2, the second affixation positions being so as to monitor cervical effacement.

A diagram, at an enlarged scale from FIG. 3b, of the affixation of the disposable probes to the cervix uteri of the pregnant human female in positions to monitor effacement is shown in FIG. 3b. The probes 13 are mounted along a same wall region, and normally on opposite sides of the wall, of the cervix os 21. When the cervix os 21 dilates (enlarges) then the distance between the probes 13 as such are attached in FIG. 3a will increase. However, during the same dilatation (enlargement) the distance between the probes 13 as such are attached in FIG. 3b will decrease. The increase is related (although not linearly) to the decrease, and vice versa. The status of the cervix os may be monitored, and interpreted, from data concerning either dilatation or effacement (or both). The normally measured, observed, monitored and interpreted quantity is dilatation, and the ensuing discussion of the function of the cervical monitor will be based on dilatation. However, a practitioner of the medical arts will understand that these and other physiological measurements are interrelated, and that the monitoring, alarming and infusing functions of the present invention are not dependent upon the particular placement of the probes 13, nor the particular path and distance that is monitored.

Figure 4A:
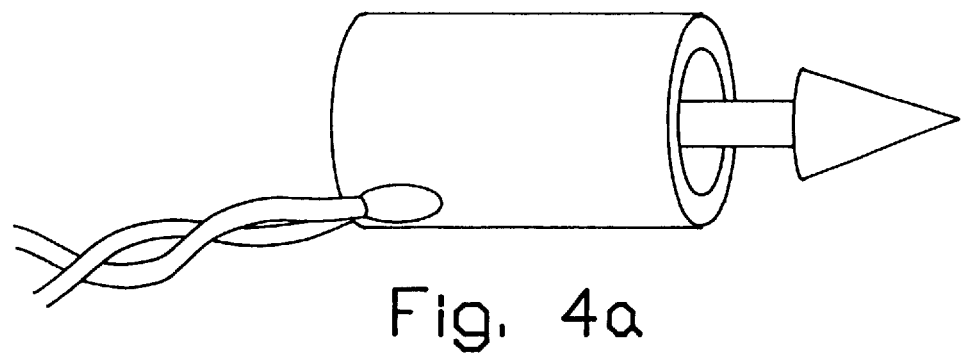
FIG. 4, consisting of FIG. 4a through FIG. 4c, show various preferred embodiments of the head of a disposable probes, two of which probes which are used with the preferred embodiment of the ambulatory cervical effacement/dilatation monitor previously seen in FIGS. 2 and 3.
Figure 4B:
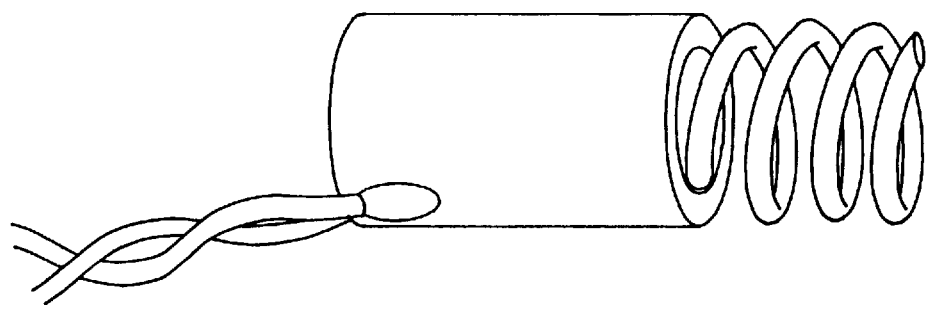
Figure 4C:
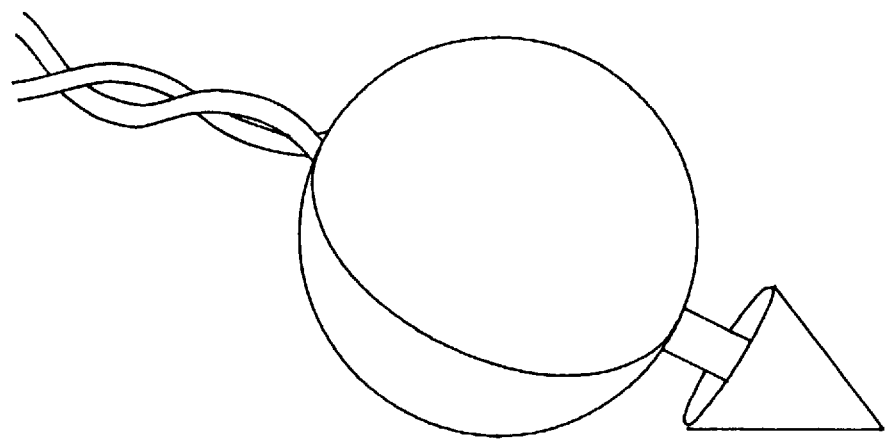

Various preferred embodiments of the head of a disposable probes, two of probes which are used with the preferred embodiment of the preferred ambulatory cervical effacement/dilatation monitor previously seen in FIGS. 2 and 3, are shown in FIG. 4, consisting of FIG. 4a through FIG. 4c. The body of the embodiments of FIGS. 4a and 4b is substantially cylindrical whereas the embodiment of FIGS. 4c is substantially spherical. The transducer of each of these two body configurations is in the substantial shapes of a three-dimensional, non-planar, bodies. This is somewhat unusual because an ultrasonic transducer is normally housed in a substantially planar parallelepiped body, typically a disk. Such need not be the case, however. The ultrasound, which is electrically produced in a crystal, will radiate from the surface of the surrounding housing, whatsoever its shape.

Each of the preferred transducer bodies shown in FIGS. 4a–4c is characterized in that ultrasound emissions from the transducer occur along a multiplicity of axis in multiple different directions. The reason that the transducers are so omnidirectional is that, when secured to the wall of the cervix uteri of human female such as by their barbed fishhook or corkscrew coil (to be discussed), the transducers are substantially insensitive to their initial placement(s) and alignment(s), and also to any directional changes occurring before or during labor. The preferred transducers serve to maintain good acoustic coupling under all conditions.

It is, or course, necessary to maintain the transducers 13 in their predetermined, fixed, locations upon the cervix os 21 so that ultrasonic transit time measurements may be performed. There are insubstantial nerve endings on the cervix os, which is also physically very robust and resilient to permanent damage. Ultrasonic probes have heretofore been attached by corkscrews, and that embodiment of a probe 13 in accordance with the present invention that is shown in FIG. 4b continues this tradition. Corkscrews are a good, and proven, means of attachment of probes to muscle, as witness cardiac pacemakers. However, there are differences between cardiac probes and ultrasonic transducers. In the former case an electrical signal is being coupled to the muscle, and a reliable continuous electrical and physical contact must be maintained therewith. In the present ultrasonic probes, understand that no electrical, nor acoustical, energy is being attempted to be coupled into the muscle (of the cervix os) through, or by, the probe attachment. There is, or course, no electrical coupling to the muscle. The acoustic coupling is, by and large, to the surrounding mucous and fluids, and the probe is not configured for coupling acoustic energy into the cervix os (if it was then should lie tight against the cervix os). The probes' attachments are simply to hold the probes in position so that they may follow the movement of the muscle, and so that the varying distance between them may be monitored.

So considering the function of the attachment of a probe 13, the barbs of the embodiments of FIGS. 4a and 4c, of like barbs in the substantial shapes of fishhooks, are preferred for some patients. Namely, the barbed probes are generally easier, and faster, to attach in patients who are sensitive to discomfort. A corkscrew probe should be unscrewed in order to remove, but a barbed probe of the design of FIGS. 4a and 4c will usually exit cleanly if simply pulled strongly. In those generally rare affixation, and locations, where a fishhook barb (not shown) better serves retention, and positioning of the probe, then the barb may be removed exactly as a fishhook is removed from the flesh of the body. Namely, the barb is worked forward to exit the surface, and is cut off as exposed. The barb-less probe is then withdrawn.

Alternatively, the entire positioning and holding of the probes may transpire by use of a flexible elastomeric annulus-shaped membrane as is taught in the companion patent application filed on the same date. The annular membrane has a shape-retentive memory and exerts a force so as to assume and to maintain a predetermined closed-loop geometric shape, normally a circle. The annular membrane fits circumferentially about the cervix os of a human female so as to hold and retain various medical instrumentation probes, an more particularly the two opposed wire-connected ultrasonic transducers of the real-time transit-time ultrasonic monitor of cervical dilatation and effacement. The annular membranae may optionally extend as a tube downwards in the vaginal canal, in the manner of a female diaphragm, as to shield the wires from the walls of the vagina. The membrane expands and contracts with such cyclical variation in the dilatation and effacement of the cervix os as occurs from the earliest onset of labor until imminent childbirth. This membrane and its held transducer probes of an ultrasonic cervimeter may be situated in place about the cervix os for prolonged periods ranging to several months, or may be placed only at the onset of full labor, for monitoring purposes.

A graph showing a calibration of the preferred ambulatory cervical effacement/dilatation monitor is shown in FIG. 5a. The calibration is performed in the controller 11 by producing in manually controllable steps successive delays such as would be indicative, if received from probes 13, of an increasing amount of separation between the probes 13. The "manually controllable steps" simply involve the stepwise rotation of a multiple position switch which, in its successive positions, couples an increasing amount of delay into the simulated probe input to the controller 11 (the schematic diagram of which controller 11 will be shown in FIGS. 6 and 7). The lowest level of the trace in the graph of FIG. 5a is indicative of a probe separation of 10 mm; the highest level of the trace is indicative of a probe separation of 60 mm. If the number of steps are carefully counted, if may be observed that the preferred resolution of the cervimeter monitor 1 is at least as small as 5 mm.

FIG. 5b is a graph showing the typical varying dilatation of the cervix uteri of a human female, or other higher primate such as a rhesus monkey, during labor. The total period shown is about thirty (30) minutes in which period twenty (20) relatively even cycles have transpired for an average cycle time of one and one-half (1½) minutes per cycle.

Figure 6:
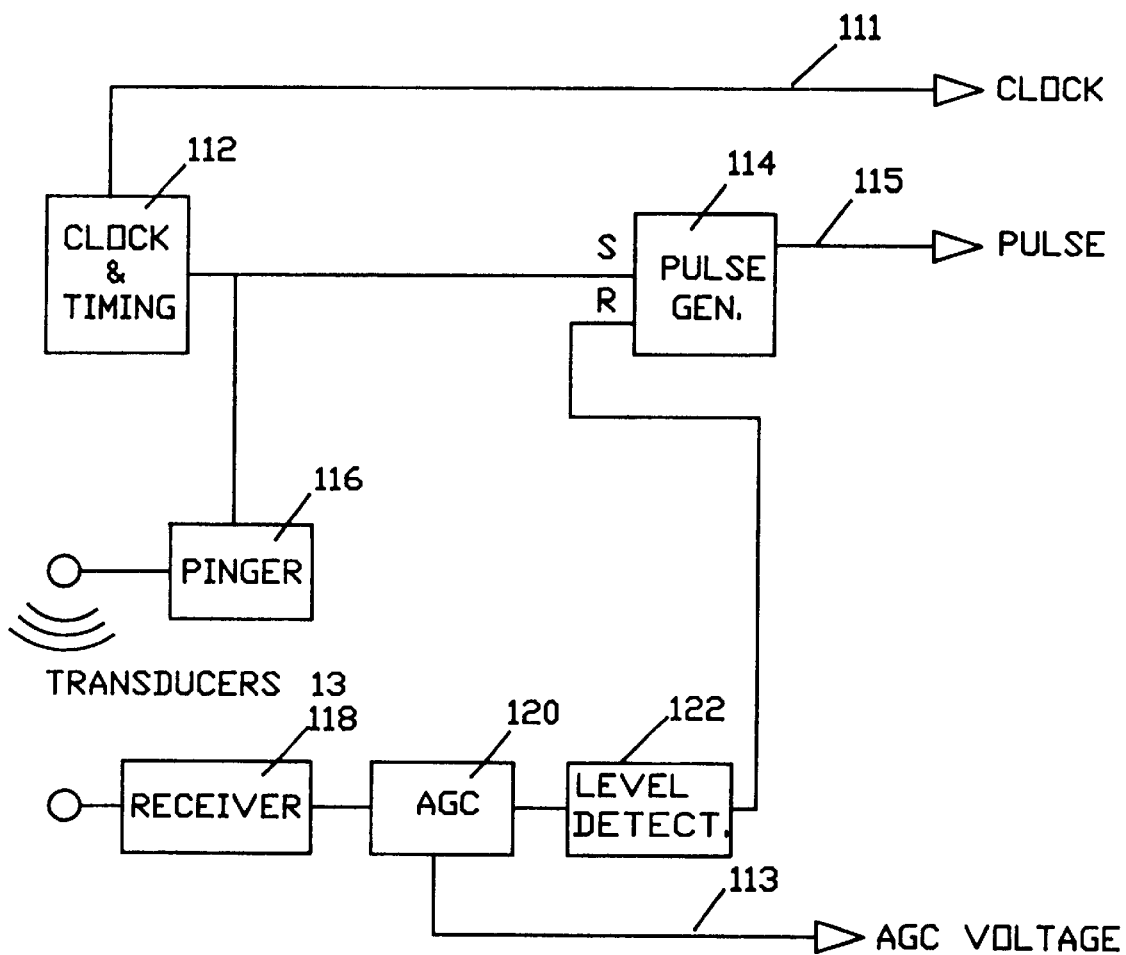
FIG. 6 is a schematic block diagram of a substantially analog first portion of the preferred embodiment of the ambulatory cervical effacement/dilatation monitor previously seen in FIG. 2.

A schematic block diagram of a substantially analog first portion 11 of the preferred ambulatory cervical effacement/dilatation monitor 1 is shown in FIG. 6. The first portion 11 is, in of itself, a complete sonomicrometer. Sonomicrometers are known in the art, and the circuit of the block diagram of FIG. 6 is simply a particular version of a sonomicrometer that is, quite obviously, adapted to the measurement task at hand in terms of (i) acoustic signal power, (ii) acoustic signal reception sensitivity, and, most importantly, (iii) the duration (not the frequency) of an acoustic signal pulse that will be appropriate to measure the distances involved in cervical dilatation, and (iv) a repetition rate of the acoustic signal pulse that will be appropriate to measure all changes in the distances involved in cervical dilatation. Notably, the frequency of the acoustic signal is an innate property of the probes, or transducers 13, which "ring" when electrically excited at their resonant frequency(ies). The probes, or transducers, 13 may suitably operate over a broad range of ultrasonic frequencies, and preferably ring at a natural resonant frequency of about 5 Mhz.

A CLOCK portion of the CLOCK AND TIMING 111 produces a fundamental 1.58 MHz frequency. This frequency is chosen because an ultrasonic acoustic pulse will travel approximately 1 millimeter in tissue—and very nearly the same in mucous or other water-based fluids—in the period of one cycle of 1.58 MHz, or 0.63 microseconds. The 1.58 Mhz signal is provided as signal CLOCK 111.

A TIMING portion of the CLOCK AND TIMING 112 produces pulses of (i) 50 microsecond duration (of 1.58 MHz signal) (ii) at a pulse repetition rate of 100 Hz. The duty cycle of the collective pulses is correspondingly (($5 \times 10^{-5}) \times 1 \times 10^2$) per second, or a low 0.5% which serves to save power. These 50 microsecond pulses at the 100 Hz. rate are applied to the set, or S, input of the PULSE GENERATOR 116 and the PINGER 114. The PINGER 116 serves as an amplifier. The 50 microsecond pulse duration is sufficient, when driven by the PINGER 114, so as to cause the driven one of the probes, or transducers, 13 to ring, producing an acoustic pulse (which gradually decays in amplitude) for an effective duration, as is such pulse is detectable at the other one of the transducers 13 and by the RECEIVER 118, of about 1 msec. (One hundred such acoustic pulses each second give an acoustic duty cycle of approximately 10%.) The duration of this acoustic pulse is, or course, not particularly important save that each pulse shall have completely died away before a next later pulse is generated. In accordance with the principles of transit time sonomicrometry, it is the delay incurred by this pulse in reaching the receiving one of the probes, or transducers, 13 that is important. Each and every pulse will incur a delay of about 0.63 microseconds per millimeter traversed.

The signal developed in the RECEIVER 118 in response to each received acoustic pulse is shaped in an automatic gain control, AGC, circuit 120 and is then subject to detection in LEVEL DETECT circuit 122. The signal AGC VOLTAGE 113 is a function of the amount of signal gain being applied in, and by, the AGC circuit 120, and will be highest when the received signal acoustic is lowest, or non-existent (as between acoustic pulses, or before an acoustic pulse has arrived). A use of such signal AGC VOLTAGE 113 will be later shown in FIG. 7. The signal output of LEVEL DETECT circuit 122 will assume a logic High condition within a few tens of nanoseconds that the acoustic pulse is received by the RECEIVER 118. The signal will, as applied to the reset, or R, input of the PULSE GENerator circuit 114, serve to reset this circuit. (It will be understood that electrical delays are small in relation to acoustic delays in a sonomicrometer.) The signal PULSE 115 arising from the PULSE GENerator circuit 114 accordingly starts with each transmission of an acoustic pulse, and ends with the reception of the same pulse. Its duration is thus indicative of the acoustic delay in the communication of the ultrasonic pulse between the two transducers 13.

FIG. 7 is a schematic block diagram of a substantially digital second, data logging and alarming, portion of the preferred embodiment of the preferred ambulatory cervical effacement/dilatation monitor 1. This data logging and alarming portion receives all three signals 111, 113, and 115 developed in the analog, sonomicrometer, portion previously seen in FIG. 6. The signal CLOCK, which is at a frequency of 1.58 Mhz, serves to increment a COUNTER 124 that is enabled for counting for the duration of signal PULSE 115. The number of counts accrued during the duration of each signal PULSE 115 is the thus the distance in millimeters that the ultrasonic acoustic signal traversed between probes 13 (shown in FIG. 6). Permitting the COUNTER 124 to read directly in millimeters avoids the necessity of a later conversion. Once the count is terminated by the logic Low condition of signal PULSE 115, the COUNTER 124 will put the accrued count onto a digital communications bus that is called DIMENSION BUS 117 because it carries the cervical dimension. The COUNTER 124 will also reset itself to zero for the next counting interval (which, in accordance with CLOCK AND TIMING 112 shown in FIG. 6, will occur in 10 milliseconds).

The current count, which is the cervical dilatation (or effacement) in millimeters, is received into a LATCH 126 and a COMPARE circuit 128. The COMPARE circuit 128 also receives a digital quantity from the PHYSIO LIMIT SET register 130. This quantity represents the greatest reasonable, real-world, change that would be expected in cervical dilatation over the time interval between successive counts, or 10 milliseconds. This quantity is equivalent to a change in cervical diameter of about 1 millimeter per second. The previous cervical measurement that was stored in LATCH 126 is compared with the current cervical measurement received via DIMENSION BUS 117, and with the maximum expected change received from PHYSIO LIMIT SET register 130 in order to make the single determination that the presently-received cervical dimension either is, or is not, reasonable. An unreasonable reading might be received, for example, due to ultrasonic noise. If the cervical dimension, as is upon the DIMENSION BUS 117, is reasonable then the input from the COMPARE circuit 128 to the AND gate 132 is a logic High, satisfying one of the two inputs to AND gate 132.

The other, remaining, input to the AND gate 132 is derived from differential amplifier 134. The signal 119 from this differential amplifier 134 will be a logic High, satisfying the remaining one of the inputs to AND gate 132, at such times as the signal AGC VOLTAGE 113 is greater than a preset signal level supplied from the reference voltage level, or LEVEL SET 136. The signal AGC VOLTAGE 113 will so be greater than the preset signal level supplied from reference voltage level SET 136 when, and upon such times, as the RECEIVER 118 (shown in FIG. 6) is not receiving an ultrasonic pulse. According to being in an interval between the reception of ultrasound, the COUNTER 124 is not incrementing, and the cervical dimension that is upon the DIMENSION BUS 117 driven from the COUNTER 124 is (momentarily) stable, and invariant. Satisfaction of the AND gate 132 will produce a logic High gating signal to the DISPLAY 138, and will cause the DISPLAY 138 to capture the cervical dimension quantity that is upon the DIMENSION BUS 117 and to display it as a vertical bar in a next successive position proceeding towards the right across a visual display area.

The display 138, if not substantially the entire data logger shown in FIG. 7, may optionally, and even preferably, based upon a microprocessor. A practitioner of the digital logic design arts will have no difficulty in accomplishing the counting and comparison functions already discussed in FIG. 7, as well as certain other functions to be discussed, in the logic and the registers of a microprogrammed microprocessor. A microprocessor may, for example, scale the cervical dimension received on DIMENSION BUS 117 in order to appropriately size, and place, a graphical display on the DISPLAY 138. Indeed, almost as soon as the practitioner of the digital logic design arts starts to think about the flexibility, and power, of a microprocessor as applied to the data logging and alarming task of FIG. 7, it is possible to realize that, other than the necessity of comparing analog signal levels in the differential amplifier 134 (and also in differential amplifier 140, yet to be discussed) and displaying data in the DISPLAY 138, veritably everything could be done in a microprocessor. In such a case FIG. 7 could be equally validly considered as a functional, as opposed to a hardware, block diagram.

The preferred implementation of the present invention is, as is shown in FIG. 7, to (i) use a microprocessor (not shown) as part of DISPLAY 138, but (ii) not to place have all such functionality as might conceivably be accomplished by the microprocessor so accomplished. This is for two reasons not immediately apparent on the face of FIG. 7. First, it is contemplated that, with an appropriate data storage memory and sequential memory addressing (not shown) that a power-consuming microprocessor and a visual display might be turned off for periods of time and from time to time, saving energy when no one cares to view historical cervical dilatation (effacement) data in the DISPLAY 138. Second, and although various alarms the development of which is yet to be discussed are shown to be communicated directly to the DISPLAY 138, and presumably to any microprocessor (not shown) lodged therein, if is very simple to understand that, by use of discrete circuits no more complex than a latch, it would be possible to register, and to sound and/or display (in the form of a light, or LED), one or more alarms without the involvement of any microprocessor, or microcoded program. Although outside the scope of the present disclosure, the data logging and alarming circuitry of FIG. 7 can thus readily be made to have (i) a reduced-power, fall back, operational mode, and/or (ii) substantially fail-safe operation.

An alarming monitor of cervical dilatation/effacement does not incur the reliability requirements of, for example, a cardiac pacemaker. If the instrument fails the patient neither aborts, nor gives birth, nor suffers any adverse effects whatsoever. However, it is anticipated that, in some pregnancies, successful live birth may be dependent upon the adequacy and continuity of the cervical monitoring, and the timely administration of all such interventions (primarily tocolytic drugs) as are indicated to be prudent and necessary as a result of such monitoring. Accordingly, the cervical dilatation (or effacement) monitor is desirably, and is, constructed as a quality instrument, with due regard by design for its potentially crucial function.

Continuing in FIG. 7, a battery (not shown), nominally of a 9 v.d.c. type which typically suffices to last at least two (2) weeks and more commonly two (2) months in continuous use, produces a battery voltage BATT VOLTS 121. This battery voltage is compared in differential amplifier 140 to the voltage output of a constant voltage circuit LEVEL SET 142. Until, an unless, the battery voltage falls below a predetermined level, normally eight (8) v.d.c., the signal ALARM 123 will be maintained a logic High level, and the DISPLAY 138 will not produce an alarm. At any such times as the battery voltage were to fall below the predetermined level the signal ALARM 123 will go to a Logic Low level, and the DISPLAY 138 will produce a visual and/or audible alarm in plenty of time to replace the battery (not shown) before power reserves are exhausted.

A comparison of the cervical dilatation (effacement) measurement as is present on the DIMENSION BUS 117 is made in, and by, COMPARE circuit 144 to a predetermined dimension that is stored in the DIMN ALARM SET register 146. The DIMN ALARM SET register 146 is intended to contain a maximum dimension in the case of evaluating cervical dilatation, or, conversely, a minimum dimension in the case of evaluating cervical effacement, which, when the cervical dimension is respectively greater than or less than the stored dimension, is indicative that labor has begun (or at least of an extreme cervical condition). The result of the comparison is communicated to OR gate 148 as a logic High signal in the event that the threshold is exceeded. The predetermined dimension that is stored in the DIMN ALARM SET register 146 is preferably adjustably so predetermined, and stored. A microprocessor (not shown, typically closely associated with DISPLAY 138) may facilitate this storage, normally of a value that is determined by the attending physician or obstetrician.

In a similar manner, another comparison of the cervical dilatation (effacement) measurement made in, and by, COMPARE circuit 152 to a predetermined dimension that is stored in the DIMN RATE ALARM SET register 152. Notably, the cervical dimension is not even transferred to the COMPARE circuit 152 until the COMPARE circuit 144 is satisfied, meaning that a threshold cervical dilatation/ effacement measurement has been exceeded. The DIMN RATE ALARM SET register 152 is intended to contain a minimum rate of the change of dimension cervical dilatation, or effacement. This quantity is involved once labor has begun (which was presumptively determined by satisfaction of COMPARE Circuit 144). If the predetermined rate of change is not exceeded then this may be indicative of problems with the progress of labor. The result of the comparison is also communicated to OR gate 148 as a logic High signal in the event that the predetermined rate of change is not exceeded. The predetermined rate of change that is stored in the DIMN RATE ALARM SET register 152 is preferably adjustably so predetermined, and stored. A microprocessor (not shown, typically closely associated with DISPLAY 138) again facilitates this storage, normally again of a value that is determined by the attending physician or obstetrician.

Satisfaction of the OR gate 148 produces a logic High signal ALARM 125, which signals received into DISPLAY 125 is used to produce a visual and/or audio alarm. The signal ALARM 125 is also routed TO INFUSION CONTROLLER, where it is used to control the infusion of the tocolytic drug by the infusion pump.

Figure 7A:
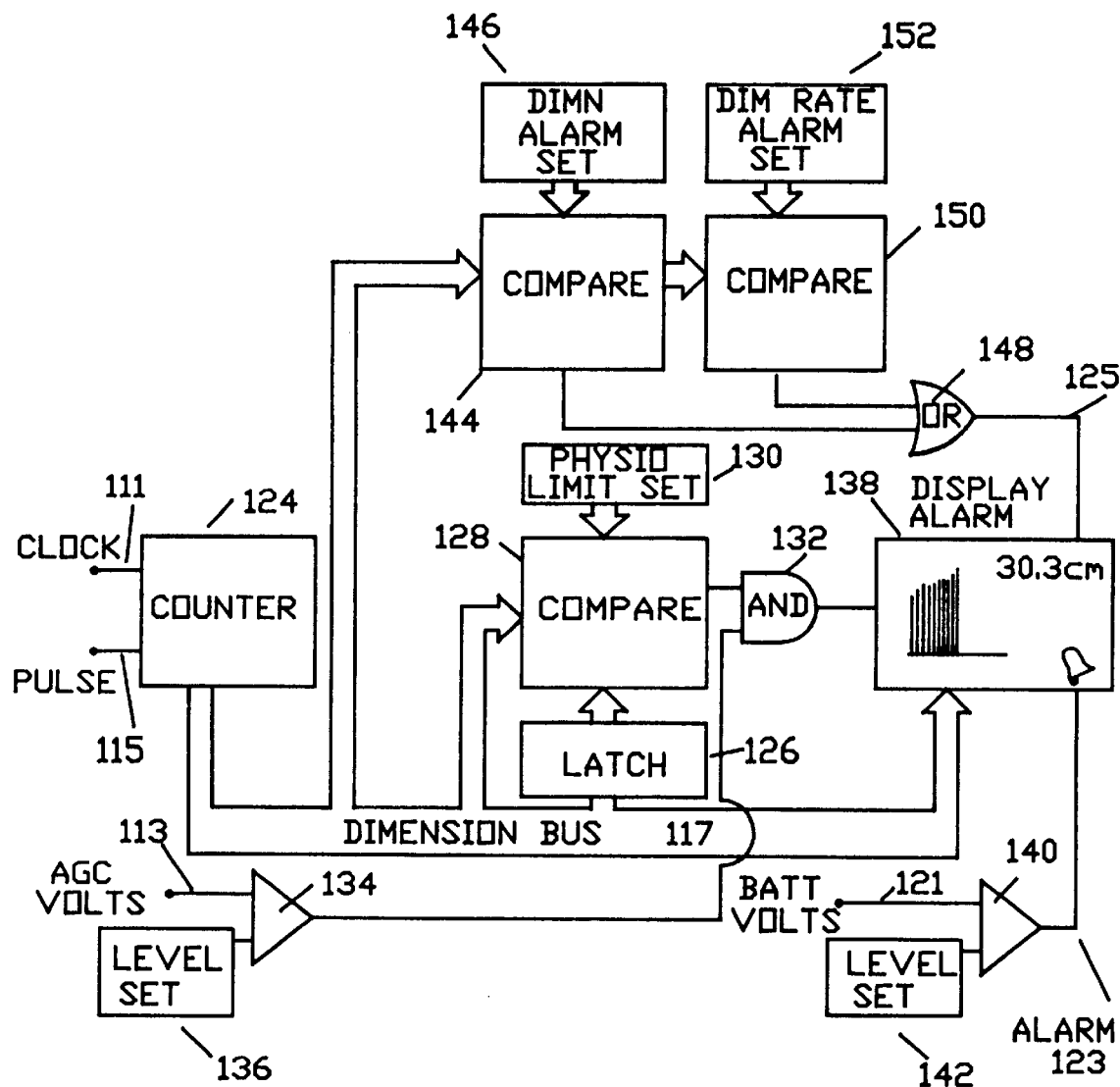
FIG. 7a is a schematic block diagram of a substantially digital second portion of the preferred embodiment of the ambulatory cervical effacement/dilatation monitor used in the system of the present invention, the analog portion of which ambulatory cervical effacement/dilatation monitor was previously seen in FIG. 6.
Figure 7B:
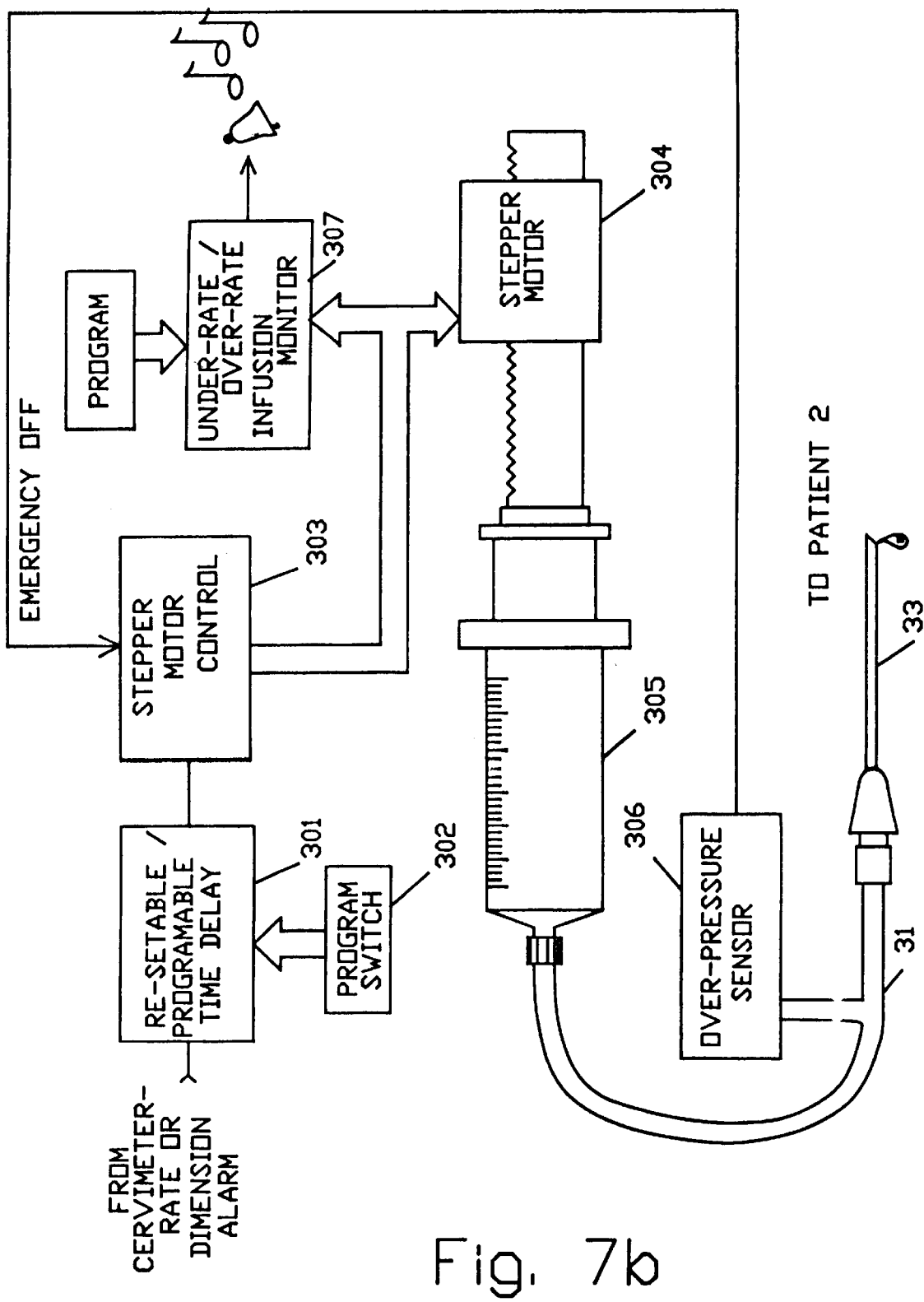
FIG. 7b is a schematic block diagram of a preferred embodiment of an ambulatory infusion pump used in the system of the present invention.

A schematic block diagram of a preferred embodiment of an ambulatory infusion pump 3 (previously seen in FIG. 2) used in the system of the present invention is shown in FIG. 7b. The signal ALARM 125 received from the OR gate 140 of the monitor 1 (shown in FIG. 7a) is delayed in a RESETTABLE PROGRAMMABLE TIME DELAY. The default value of the delay is five minutes, which may be set higher or lower by action of PROGRAM SWITCH 302. The delayed signal ALARM is routed to STEPPER MOTOR CONTROL 303, the details of which are further diagrammed in FIG. 7c. The STEPPER MOTOR CONTROL 303 acts to control the STEPPER MOTOR 304 to inject first a bolus, and then a continuing smaller infusion, of a tocolytic drug stored in reservoir 305 through the catheter 31 (also shown in FIG. 2) and the needle 33 into the woman patient 2 (shown in FIG. 2). An OVER-PRESSURE SENSOR detects any failure of flow, and feeds back to the STEPPER MOTOR CONTROL 303. Likewise, and UNDER RATE/ OVER RATE INFUSION MONITOR 307 directly monitors the output control signal of the STEPPER MOTOR CONTROL 303 as is transmitted to the STEPPER MOTOR 304, and sounds an alarm (different from the alarm of monitor 1) if, and when, and untoward infusion condition is detected.

Figure 7C:
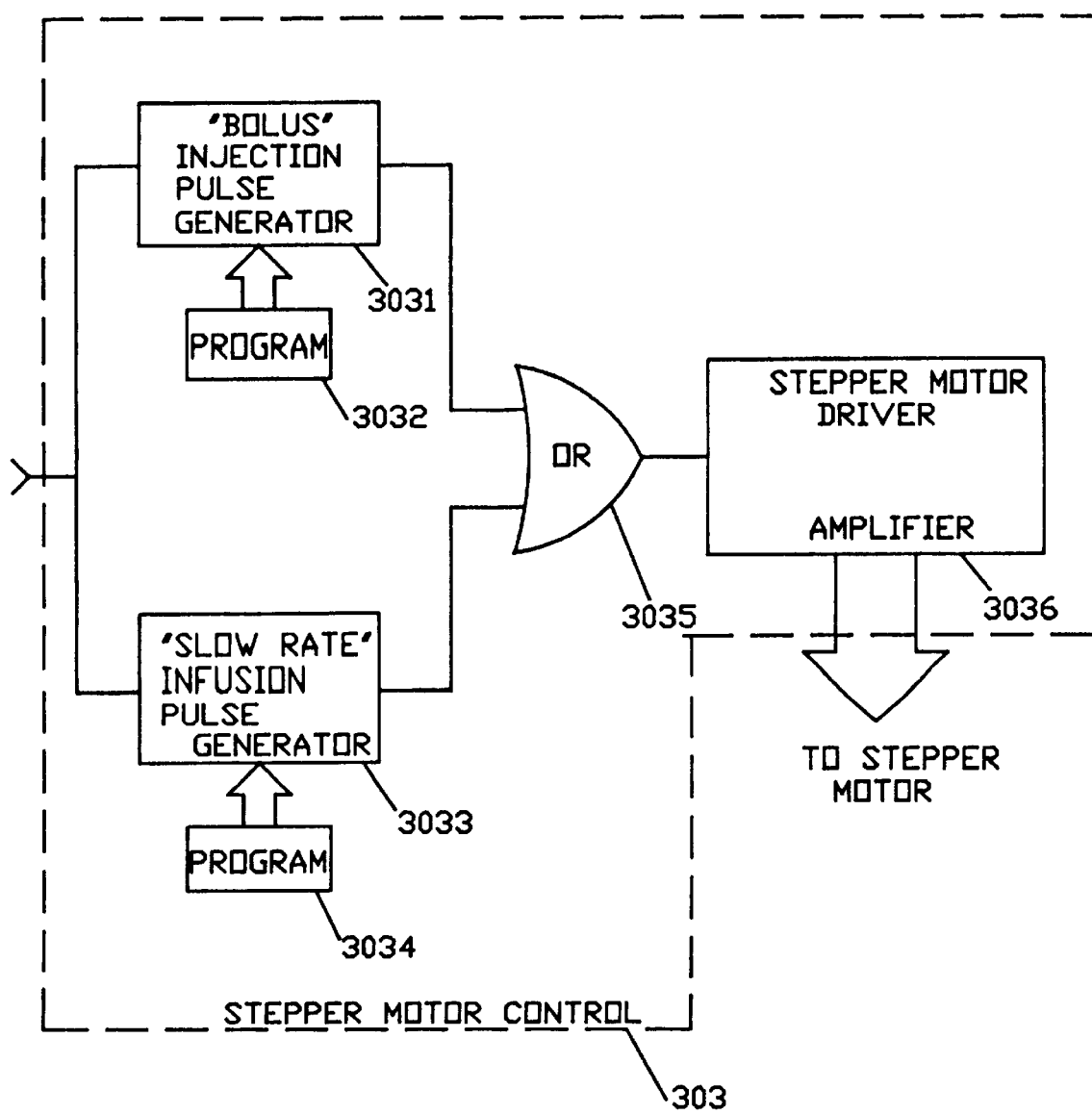
FIG. 7c is a schematic block diagram of the stepper motor control of the preferred embodiment of the ambulatory infusion pump used in the system of the present invention previously seen in FIG. 7b.

A schematic block diagram of the preferred STEPPER MOTOR CONTROL 303 of the preferred embodiment of the ambulatory infusion pump 3 (previously seen in FIG. 1) used in the system of the present invention is shown in FIG. 7c. A "BOLUS" INJECTION PULSE GENERATOR 3031 operating under control of a PROGRAM 3032 produces a first, relatively larger and relatively shorter, drive pulse the effect of which will be shown in FIG. 10c. A "SLOW" RATE INJECTION PULSE GENERATOR 3033 operating under control of a PROGRAM 3034 produces a second, relatively smaller and relatively longer, drive pulse the effect of which will be shown in FIG. 10*c*. The two drive pulses are combined in OR gate 3035 and amplified in STEPPER MOTOR DRIVER AMPLIFIER 3036. The amplified pulses are then routed to, and used to drive, the STEPPER MOTOR 304 (shown in FIG. 7*b*) to inject the tocolytic drug.

Figure 8:
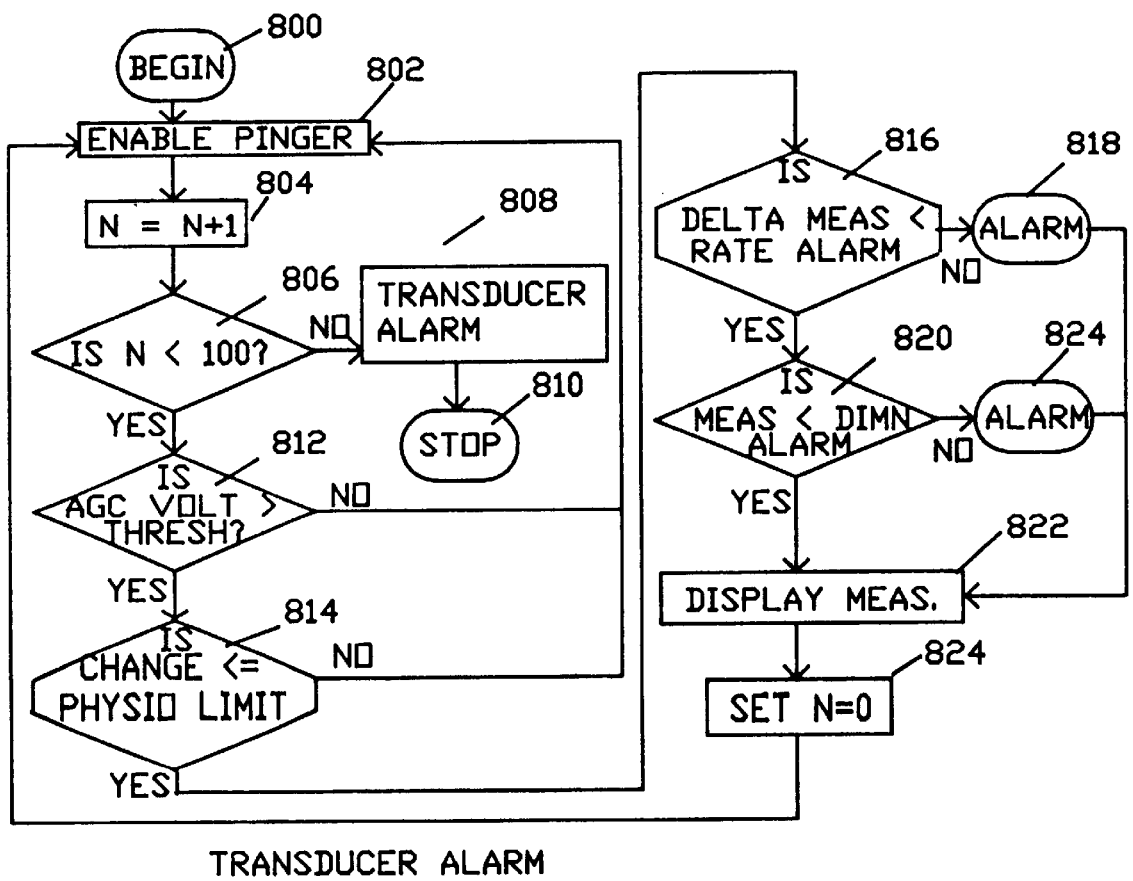
FIG. 8 is a flow chart of the function of the preferred embodiment of the ambulatory cervical effacement/ dilatation monitor used in the system of the present invention previously seen in perspective view in FIG. 2, and in schematic block diagram in FIGS. 6 and 7.

A flow chart of the function of the preferred embodiment of the ambulatory cervical effacement/dilatation monitor used in the system of the present invention previously seen in perspective view in FIG. 2, and in schematic block diagram in FIGS. 6 and 7, is shown in FIG. 8. The flow chart is, as well as being functional, suitable to serve as the flow chart of a sequential controller, particularly (but not necessarily) including a microprogrammed microprocessor. It will be recognized by a practitioner of the digital circuit design arts that the relative simplicity of the functional control block diagrammed in FIG. 8 may be accomplished by, and in, many alternative circuit implementations including, but not limited to, a microprogrammed microprocessor circuit.

The function of the ambulatory cervical effacement/dilatation monitor 1 commences with BEGIN block 800 upon application of power, and proceeds to commencing ultrasound transmission with ENABLE PINGER block 802. An ultrasound, or "ping", transmission count N is incremented in block 804, and inquiry is made as to whether this count has exceeded 100 in block 806. As will be developed in the further explanation of FIG. 8, it is a highly abnormal condition, indicating that at least 101 ultrasound pulses have been transmitted with no intervening receptions, if N is greater than 100. In such an eventuality, transducer or transducer interconnect hardware failure is indicated, and a TRANSDUCER ALARM is sounded in block 808 and the monitor 1 brought to a STOP in block 810.

Normally block 806 is satisfied, and the inquiry as to whether the Automatic Gain Control (AGC) voltage is greater than a threshold—AGC VOLT>THRESHOLD—is made in block 812. If not, no ultrasonic pulse has as yet been received, and the transmission process is re-enabled commencing with block 802.

If a received pulse is detected in block 812, then a reasonability check on the detected delay is performed in block 814. It is therein inquired as to whether the detected change is within the physiological limits of the human subject, IS CHANGE <=PHYSIO LIMIT? In the event that it is not, process error has occurred and the transmission process is again re-enabled commencing with block 802.

If, however, all status and reasonableness checks of blocks 806, 812 and 814 are satisfied, flock 816 is entered to assess whether the change in measurements dictates a rate alarm. If the measurement change does not exceed the predetermined alarm threshold, then DELTA MEAS<RATE ALARM? is answered yes and block 820 is entered. Should, however, the measurement change exceed the predetermined alarm threshold, then an ALARM is indicated in block 818.

Similarly, block 820 is entered to assess whether the absolute magnitude of the measurement dictates an alarm. If the measurement change does not exceed a predetermined alarm threshold dimension, then MEAS<DIMN ALARM? is answered yes and block 822 is entered. Should, however, the measured dimension exceed the predetermined alarm threshold dimension, then an ALARM is indicated in block 824.

Whether a dimension, or a dimensional change, has occasioned the respective ALARM of block 824, of or block 818, or not, the block 822 DISPLAY MEAS is always entered and the measurement displayed. The count number of the ultrasound transmission is thereafter reset to zero—SET N=0—in block 824, and the entire loop process re-entered at block 802.

Figure 9:
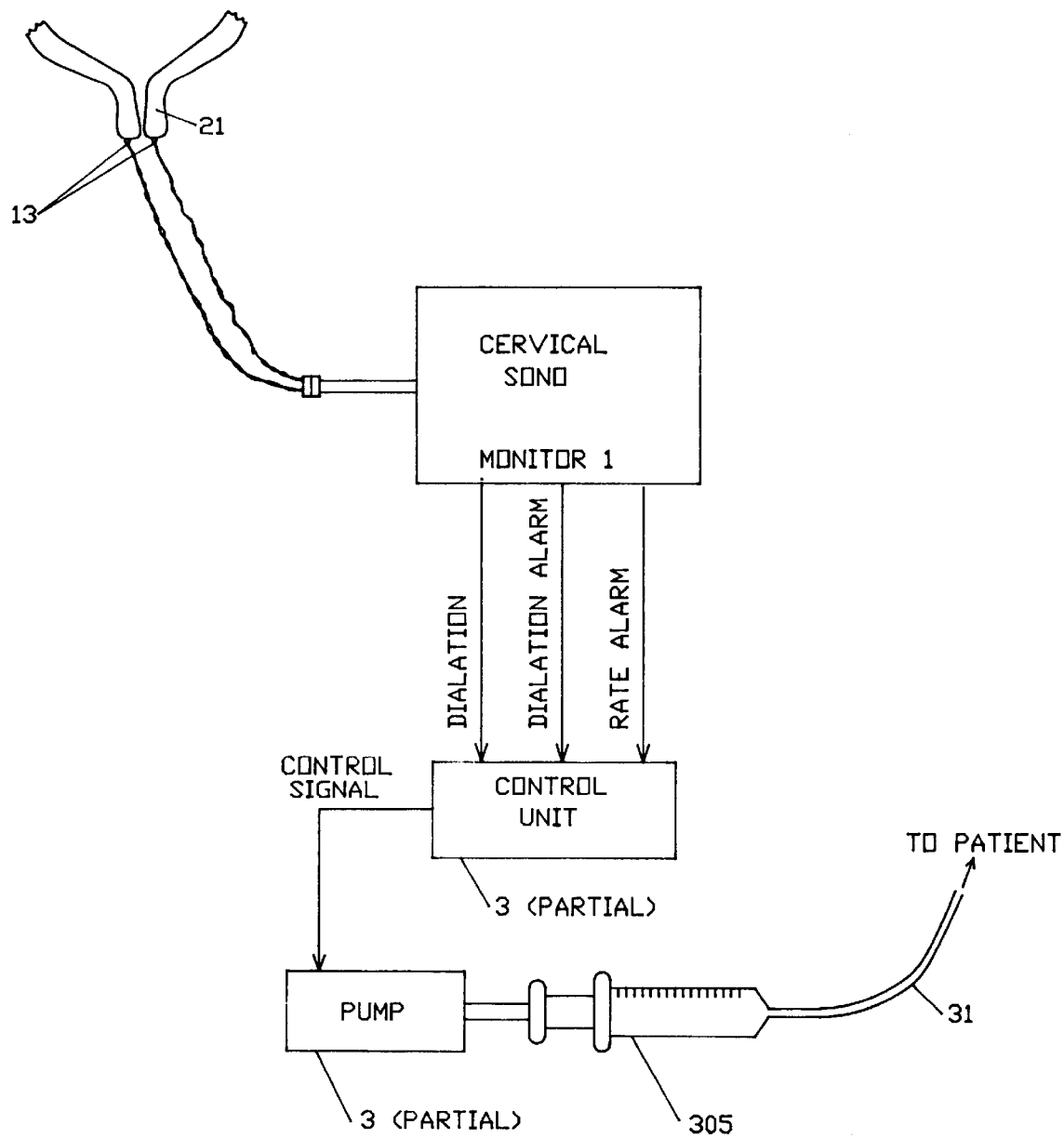
FIG. 9 is a schematic block diagram of a preferred embodiment of the complete system of the present invention for infusing of tocolytic drugs in response to the onset of premature labor detected by ultrasonic monitoring of the dilatation and/or effacement of the cervix os, the block diagram being coupled with a diagrammatic representation of a placement of ultrasonic transducers at and about the cervix os.

A schematic block diagram of a preferred embodiment of the complete system of the present invention for infusing of tocolytic drugs in response to the onset of premature labor detected by ultrasonic monitoring of the dilatation and/or effacement of the cervix os is shown in FIG. 9. FIG. 9 also shows a diagrammatic representation of a placement of ultrasonic transducers 13 at and about the cervix os 21. The signals from transducers 13 are received at the CERVICAL SONOMICROMETER—MONITOR 1 (which is but a lengthened, and more descriptive, name for the monitor 1 previously seen in FIG. 2). The CERVICAL SONOMICROMETER—MONITOR 1 ultimately conceptually produces signals representative of cervical DIMENSION, a cervical DIMENSION ALARM and a cervical RATE ALARM (which conceptual signals combined are the same as the real, physical, signal ALARM 125 that is shown in FIGS. 7*a* and 7*b*). The reason the DIMENSION and the DIMENSION RATE conceptual signals are separated, and distinct, in FIG. 9 is to better illustrate that the system, and the CERVICAL SONOMICROMETER—MONITOR 1 is firmly in possession of both quantities. In response to control from the CERVICAL SONOMICROMETER—MONITOR 1, the CONTROL UNIT 3 (partial) and the INFUSION PUMP 3 (partial)—which were combined as infusion pump 3 in FIG. 2—serve to further time, and control, the ejection of a tocolytic drug from the reservoir 305 (also shown in FIG. 7*b*) through the catheter 31 into the Patient 2 (shown in FIG. 2). Insofar as the injection of the tocolytic drug ultimately effects the ultrasonically monitored dilatation/effacement, and the cyclical variations on dilatation/effacement, of the cervix os 21, the system of the present invention diagrammed in FIG. 9 is closed loop.

Figure 10A:
FIGS. 10a through 10c are graphs showing the timing of certain control signals, and the resulting administration of tocolytic drugs by the infusion pump under control of the software program running in the ultrasonic monitor of the cervix os in the system of the present invention previously seen in FIG. 9, the programmed administration being in response to the dilatation and/or effacement of the cervix os sensed and interpreted by the monitor.
Figure 10B:
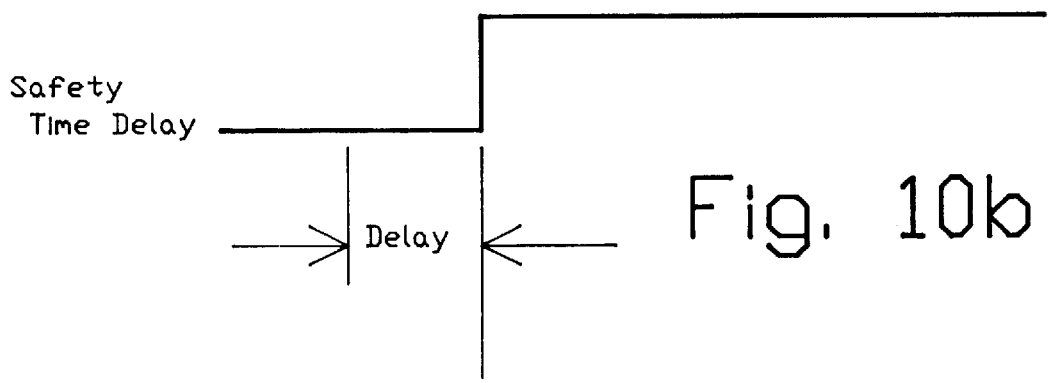
Figure 10C:
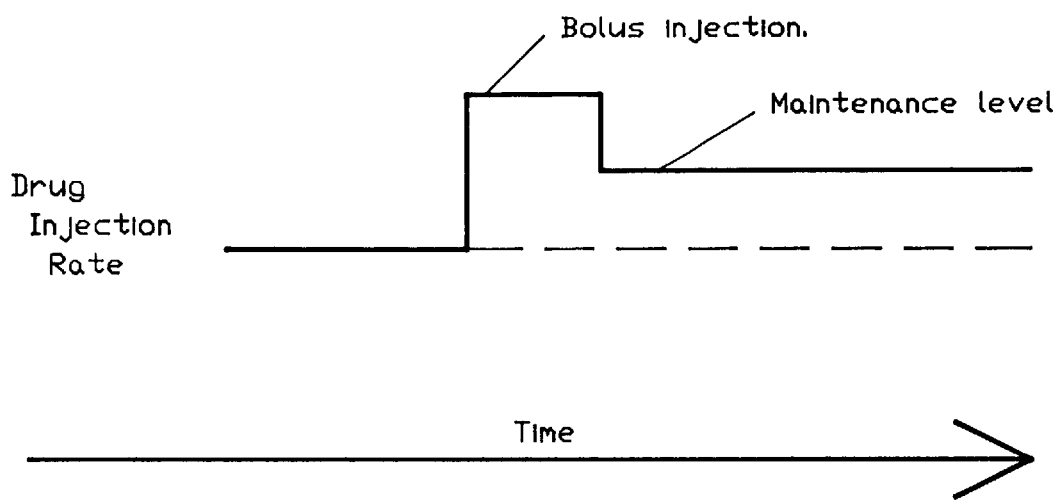

Graphs showing the timing of certain control signals, and the resulting administration of tocolytic drugs by the infusion pump under control of the software program running in the ultrasonic monitor of the cervix os in the system of the present invention previously seen in FIG. 9, are shown in FIGS. 10*a* through 10*c*. The signal ALARM 125, previously seen in FIGS. 7*a* and 7*b*, that represents the detected onset of labor by the monitor 1 (shown in FIG. 9) is graphed in FIG. 10*a*. After the variably programmed time delay of RESETTABLE PROGRAMMABLE TIME DELAY 301 shown in FIG. 7*b*, the signal SAFETY TIME DELAY also goes to a logic High, or true, condition. This is the signal used to control the STEPPER MOTOR CONTROL, and the infusion, that are block diagrammed in FIGS. 7*b* and 7*c*. The resulting drug injection rate is, under the programmed control of the STEPPER MOTOR CONTROL 303 as was previously shown in FIGS. 7*b* and 7*c*, preferably as shown in FIG. 10*c*. An initial BOLUS is injected, followed by the steady slower injection rate labeled MAINTENANCE. The overall programmed injection, and administration, of the tocolytic drug is in response to the dilatation and/or effacement of the cervix os as was sensed, monitored and interpreted by the monitor 1.

In accordance with the preceding explanation, many variations and alterations of the preferred embodiment of the present invention will suggest themselves to a practitioner of the electronic medical equipment design arts. For example, many more separate, and detailed, alarms could be made contingent upon conditions which may be quite intricate, and convolute. For example, the display, and history display, could be of alternative intervals and epochs. For example, the infusion of tocolytic drugs could be periodic, and at a low level, as well as episodic based on cervical monitoring. For example, the infusion of tocolytic drugs could be under control of a modem connection to a physician's office, or in response to other, additional, sensed stimuli or conditions other than just cervical dilatation.

In accordance with these and other possible variations and adaptations of the present invention, the scope of the invention should be determined in accordance with the following claims, only, and not solely in accordance with that embodiment within which the invention has been taught.

What is claimed is:

1. A system for the postponement of labor/spontaneous abortion in a pregnant human female patient, the system comprising:

a ultrasonic cervimeter monitor of the dilatation and/or effacement of the cervix os of a pregnant human female patient; and an infusion pump responsive to certain conditions indicative of labor sensed by the monitor to infuse a tocolytic drug into the pregnant human female patient.

2. The system according to claim 1 wherein the ultrasonic cervimeter monitor comprises:

an ultrasonic transit-time cervimeter.

3. The system according to claim 1 wherein the monitor comprises:

a transducer in the substantial shape of a three-dimensional, non-planar, body characterized in that ultrasound emissions from the transducer are along a multiplicity of axis in multiple different directions;

means for securing the transducer to the wall of the cervix uteri of human female;

an ultrasonic transit-time cervimeter; and an electrical wire connecting between the transducer in its position secured to the wall of the cervix and an ultrasonic transit time cervimeter in a location exterior to human female's body.

4. The system according to claim 1 wherein the infusion pump comprises:

an electrical infusion pump; and a battery for powering the electrical infusion pump.

5. The system according to claim 4 wherein the reservoir is of a beta-sympathomimetic tocolytic drug from the group consisting of Terbutaline and Ritodrine.

6. A system for the postponement of labor/spontaneous abortion in a pregnant human female patient, the system comprising:

an ultrasonic transmitter in the substantial shape of a three-dimensional, non-planar, body characterized in that ultrasound is emitted from the transmitter along a multiplicity of axis in multiple different directions;

an ultrasonic receiver in the substantial shape of a three-dimensional, non-planar, body characterized in that ultrasound is received along a multiplicity of axis from multiple different directions;

a means for securing the ultrasonic transmitter, and also the ultrasonic receiver, to the wall of the cervix uteri of human female at spaced apart positions so that a straight line ultrasonic acoustic path at least partially through the cervix exists between the ultrasonic transmitter and the ultrasonic receiver, the path being simultaneously along at least one ultrasound emission axis of the ultrasonic transmitter and at least one ultrasound reception axis of the ultrasonic receiver;

an ultrasonic transit time micrometer for detecting a delay in the propagation of ultrasound from the ultrasonic transmitter to the ultrasonic receiver as an indication of the dilatation of the cervix uteri;

electrical wires connecting both the ultrasonic transmitter and the ultrasonic receiver in their positions secured to the wall of the cervix to the ultrasonic transit time micrometer; and an infusion pump responsive to certain conditions indicative of labor sensed by the ultrasonic transit time micrometer to infuse a tocolytic drug into the pregnant human female patient.

7. The ultrasonic transit time cervimeter according to claim 6 wherein at least one of the ultrasonic transmitter and the ultrasonic receiver comprises:

an ultrasonic transducer in the substantial shape of a cylinder.

8. The ultrasonic transit time cervimeter according to claim 6 wherein at least one of the ultrasonic transmitter and the ultrasonic receiver comprises:

an ultrasonic transducer in the substantial shape of a sphere.

9. The ultrasonic transit time cervimeter according to claim 6 wherein the ultrasonic transit time micrometer comprises:

a first alarm circuit for causing an alarm upon such times as the detected ultrasound delay varies sufficiently regularly over time so as to, by indicating a corresponding temporally regular variation in the dilatation of the cervix uteri, mark the onset of labor.

10. The ultrasonic transit time cervimeter according to claim 9 wherein the ultrasonic transit time micrometer comprises:

another, second, alarm, circuit enabled only after actuation of the first alarm and upon such times as the detected ultrasound delay exhibits an insufficient variation over time so as to, by indicating a lack of temporal variation in the dilatation of the cervix uteri, mark the onset of problems with labor.

11. The ultrasonic transit time cervimeter according to claim 6 wherein the ultrasonic transit time micrometer comprises:

an alarm upon circuit for causing an alarm upon such times as the detected ultrasound delay is sufficiently great so as to indicate that the dilatation of the cervix uteri has exceeded a predetermined size.

12. An ultrasonic transit time cervical dilatation monitor comprising:

an ultrasonic transmitter;

an ultrasonic receiver;

a means for securing the ultrasonic transmitter, and also the ultrasonic receiver, to the wall of the cervix uteri of human female at spaced apart positions so that an ultrasonic acoustic path at least partially through the cervix exists between the ultrasonic transmitter and the ultrasonic receiver;

an ultrasonic transit time micrometer, connected to both the ultrasonic transmitter and the ultrasonic receiver in their positions secured to the wall of the cervix, for detecting a delay in the propagation of ultrasound from the ultrasonic transmitter to the ultrasonic receiver as an indication of the dilatation of the cervix uteri;

a monitor of the indicated dilatation of the cervix uteri for causing an alarm if a predetermined condition of dilatation is detected; and an infusion pump responsive to certain conditions indicative of labor sensed by the monitor to infuse a tocolytic drug into the pregnant human female patient.

13. The ultrasonic transit time cervical dilatation monitor according to claim 12 wherein the monitor of the indicated dilatation of the cervix uteri is causing the alarm upon the monitoring of regular temporal cycles in the dilatation of the cervix, indicating the onset of labor.

14. The ultrasonic transit time cervical dilatation monitor according to claim 12 wherein the monitor of the indicated dilatation of the cervix uteri is causing the alarm upon a cessation of any temporal cycles in the dilatation of the cervix, indicating an onset of problems once labor has commenced.

15. The ultrasonic transit time cervical dilatation monitor according to claim 12 wherein the monitor of the indicated dilatation of the cervix uteri is causing the alarm upon the dilatation of the cervix exceeding a predetermined distance.

16. An automated method of infusing a tocolytic drug into a pregnant human female patient in response to monitoring of cervical dilatation comprising:

securing an ultrasonic transmitter and an ultrasonic receiver at spaced-apart positions upon the wall of the cervix uteri;

energizing the secured ultrasonic transmitter and ultrasonic receiver with and by an ultrasonic transit time micrometer;

detecting the ultrasound propagation transit time from the ultrasonic transmitter to the ultrasonic receiver with and by use of the ultrasonic transit time micrometer in order to provide an indication of the corresponding dilatation of the cervix uteri;

electronically monitoring the detected transit time, and the indicated dilatation of the cervix uteri corresponding to the detected transit time, in order so as to sound an alarm if a predetermined condition of dilatation is detected; and infusing a tocolytic drug into the pregnant human female patient in response to certain conditions indicative of labor detected by the electronic monitoring.

17. The automated method of infusing a tocolytic drug into a pregnant human female patient in response to monitoring of cervical dilatation according to claim 16 wherein the electronically monitoring is of a detected transit time, and of a correspondingly indicated dilatation, that marks the onset of labor.

18. The automated method of infusing a tocolytic drug into a pregnant human female patient in response to monitoring of cervical dilatation according to claim 16 wherein the electronically monitoring is of detected delay, and of a correspondingly indicated dilatation, that marks, once labor has commenced, the onset of problems with labor.

19. The automated method of infusing a tocolytic drug into a pregnant human female patient in response to monitoring of cervical dilatation according to claim 16 wherein the electronically monitoring is of detected delay, and correspondingly indicated dilatation, so as mark that the dilatation of the cervix uteri has exceeded a predetermined distance.

20. The automated method of infusing a tocolytic drug into a pregnant human female patient in response to monitoring of cervical dilatation according to claim 16 wherein the securing of the ultrasonic transmitter and the ultrasonic receiver is at spaced-apart positions between a first point upon an interior wall of the cervix uteri and a second point, the second point radially disposed radially outwardly from the first point along an extension of an imaginary vector between an imaginary central axis of the cervix uteri and the first point; and wherein the detecting is of the delay in the propagation transit time of ultrasound from the first point to the second point along an imaginary radius of the cervix uteri.

21. A real-time system for the infusing of a tocolytic drug into a pregnant human female patient in response to monitoring of cervical dilatation of the cervix uteri, the system comprising;

an ultrasonic transmitter;

an ultrasonic receiver;

a means for securing the ultrasonic transmitter, and also the ultrasonic receiver, to the wall of the cervix uteri of human female at spaced apart positions so that a straight line ultrasonic acoustic path at least partially within the cervix exists between the ultrasonic transmitter and the ultrasonic receiver; and a case suitable for attachment to the body containing an ultrasonic transit time micrometer, electrically connected to both the ultrasonic transmitter and the ultrasonic receiver in their positions secured to the wall of the cervix, for detecting a delay in the propagation of ultrasound from the ultrasonic transmitter to the ultrasonic receiver as an indication of the dilatation of the cervix uteri, a memory for storing the delays as are detected over time as an indication of the dilatation of the cervix uteri over time, and a display for displaying at times each of the present dilatation of the cervix uteri, and also the dilatation of the cervix uteri over time; and an infusion pump responsive to certain conditions indicative of labor sensed by the ultrasonic transit time micrometer to infuse a tocolytic drug into the pregnant human female patient.

22. The system according to claim 21 further comprising:

an alarm circuit for alarming if the indicated dilatation of the cervix uteri equals a predetermined condition.

23. The system according to claim 21 wherein the alarm circuit is further for alarming if the indicated history of the dilatation of the cervix uteri equals a predetermined condition.

* * * * *